United States Patent
Bornzin et al.

(10) Patent No.: US 8,700,181 B2
(45) Date of Patent: Apr. 15, 2014

(54) SINGLE-CHAMBER LEADLESS INTRA-CARDIAC MEDICAL DEVICE WITH DUAL-CHAMBER FUNCTIONALITY AND SHAPED STABILIZATION INTRA-CARDIAC EXTENSION

(75) Inventors: Gene A. Bornzin, Simi Valley, CA (US); Xiaoyi Min, Thousand Oaks, CA (US); John W. Poore, South Pasadena, CA (US); Zoltan Somogyi, Simi Valley, CA (US); Didier Theret, Porter Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 100 days.

(21) Appl. No.: 13/352,101

(22) Filed: Jan. 17, 2012

(65) Prior Publication Data
US 2013/0116740 A1    May 9, 2013

Related U.S. Application Data

(60) Provisional application No. 61/555,390, filed on Nov. 3, 2011.

(51) Int. Cl.
*A61N 1/362*    (2006.01)
(52) U.S. Cl.
USPC .............................. 607/126; 607/9; 607/119
(58) Field of Classification Search
USPC .............................................. 607/9, 119, 126
See application file for complete search history.

(56) References Cited

U.S. PATENT DOCUMENTS

| | | |
|---|---|---|
| 3,835,864 A | 9/1974 | Rasor et al. |
| 3,835,869 A | 9/1974 | Newman et al. |
| 3,943,936 A | 3/1976 | Rasor et al. |
| 4,987,897 A | 1/1991 | Funke |
| 5,193,540 A | 3/1993 | Schulman et al. |
| 5,358,514 A | 10/1994 | Schulman et al. |
| 5,405,367 A | 4/1995 | Schulman et al. |
| 5,411,535 A | 5/1995 | Fujii et al. |
| 5,487,758 A | 1/1996 | Hoegnelid et al. |
| 5,545,201 A | 8/1996 | Helland et al. |
| 5,679,022 A | 10/1997 | Cappa et al. |
| 5,814,089 A | 9/1998 | Stokes et al. |

(Continued)

FOREIGN PATENT DOCUMENTS

| | | |
|---|---|---|
| EP | 1844812 A1 | 10/2007 |
| WO | 2005092431 A1 | 10/2005 |

(Continued)

OTHER PUBLICATIONS

Asirvatham, Samuel J. MD et al., "Intramyocardial Pacing and Sensing for the Enhancement of Cardiac Stimulation and Sensing Specificity," PACE. 2007;30:748-754.

(Continued)

*Primary Examiner* — Christopher D Koharski
*Assistant Examiner* — Michael Carey

(57) ABSTRACT

A leadless intra-cardiac medical device (LIMD) configured to be implanted entirely within a heart of a patient includes a housing configured to be securely attached to an interior wall portion of a chamber of the heart, and a stabilizing intra-cardiac (IC) device extension connected to the housing. The stabilizing IC device extension may include a stabilizer arm, and/or an appendage arm, or an elongated body or a loop member configured to be passively secured within the heart.

9 Claims, 26 Drawing Sheets

(56) References Cited

U.S. PATENT DOCUMENTS

| | | | |
|---|---|---|---|
| 6,141,588 | A | 10/2000 | Cox et al. |
| 6,164,284 | A | 12/2000 | Schulman et al. |
| 6,181,965 | B1 | 1/2001 | Loeb et al. |
| 6,185,452 | B1 | 2/2001 | Schulman et al. |
| 6,208,894 | B1 | 3/2001 | Schulman et al. |
| 6,434,428 | B1 | 8/2002 | Sloman et al. |
| 6,754,536 | B2 | 6/2004 | Swoyer et al. |
| 7,047,076 | B1 | 5/2006 | Li et al. |
| 7,082,336 | B2 | 7/2006 | Ransbury et al. |
| 7,114,502 | B2 | 10/2006 | Schulman et al. |
| 7,363,087 | B2 | 4/2008 | Nghiem et al. |
| 7,383,091 | B1 | 6/2008 | Chitre et al. |
| 7,513,257 | B2 | 4/2009 | Schulman et al. |
| 7,565,195 | B1 | 7/2009 | Kroll et al. |
| 7,634,313 | B1 | 12/2009 | Kroll et al. |
| 7,643,872 | B2 | 1/2010 | Min et al. |
| 7,801,626 | B2 | 9/2010 | Moser |
| 7,860,570 | B2 * | 12/2010 | Whitehurst et al. ............ 607/46 |
| 7,894,915 | B1 | 2/2011 | Chitre et al. |
| 7,899,555 | B2 | 3/2011 | Morgan et al. |
| 7,937,148 | B2 | 5/2011 | Jacobson |
| 7,945,333 | B2 | 5/2011 | Jacobson |
| 8,010,209 | B2 * | 8/2011 | Jacobson ...................... 607/119 |
| 8,032,219 | B2 | 10/2011 | Neumann et al. |
| 2004/0015204 | A1 | 1/2004 | Whitehurst et al. |
| 2004/0015205 | A1 | 1/2004 | Whitehurst et al. |
| 2004/0147973 | A1 | 7/2004 | Hauser |
| 2006/0009831 | A1 | 1/2006 | Lau et al. |
| 2006/0135999 | A1 | 6/2006 | Bodner et al. |
| 2007/0055310 | A1 | 3/2007 | Lau |
| 2007/0088396 | A1 | 4/2007 | Jacobson |
| 2007/0088400 | A1 | 4/2007 | Jacobson |
| 2008/0097566 | A1 | 4/2008 | Colliou |
| 2008/0255647 | A1 | 10/2008 | Jensen et al. |
| 2009/0082828 | A1 | 3/2009 | Ostroff |
| 2009/0299433 | A1 | 12/2009 | Dingman et al. |
| 2010/0010381 | A1 | 1/2010 | Skelton et al. |
| 2010/0198288 | A1 * | 8/2010 | Ostroff .............................. 607/9 |
| 2011/0071586 | A1 | 3/2011 | Jacobson |
| 2011/0077708 | A1 | 3/2011 | Ostroff |
| 2011/0208260 | A1 | 8/2011 | Jacobson |
| 2011/0218587 | A1 | 9/2011 | Jacobson |
| 2011/0238077 | A1 | 9/2011 | Wenger |
| 2011/0251660 | A1 | 10/2011 | Griswold |
| 2011/0251662 | A1 | 10/2011 | Griswold et al. |

FOREIGN PATENT DOCUMENTS

| | | | |
|---|---|---|---|
| WO | 2007047681 | A2 | 4/2007 |
| WO | 2007047681 | A3 | 9/2008 |
| WO | 2009039400 | A1 | 3/2009 |
| WO | 2009078751 | A1 | 6/2009 |
| WO | 2010088687 | A1 | 8/2010 |

OTHER PUBLICATIONS

Brinker, Jeffrey A., "Endocardial Pacing Leads: The Good, the Bad, and the Ugly," PACE. 1995;18(Pt 1):953-954.

Calvagna, Giuseppe M. et al., "A complication of pacemaker lead extraction: pulmonary embolization of an electrode fragment," Europace. 2010;12:613.

Da Costa, Sergio Sidney Do Carmo et al., "Incidence and Risk Factors of Upper Extremity Deep Vein Lesions After Permanent Transvenous Pacemaker Implant: A 6-Month Follow-up Prospective Study," PACE. 2002;25:1301-1306.

Hauser, Robert G. et al., "Deaths and cardiovascular injuries due to device-assisted implantable cardioverter-defibrillator and pacemaker lead extraction," Europace. 2010;12:395-401.

Heaven, D.J. et al., "Pacemaker lead related tricuspid stenosis: a report of two cases," Heart. 2000;83:351-352.

Henz, Benhur D. MD et al., "Synchronous Ventricular Pacing without Crossing the tricuspid Valve or Entering the Coronary Sinus—Preliminary Results," J Cardiovasc Electrophysiol. Dec. 2009;20:1391-1397.

Hesselson, Aaron B. Bsee et al., "Deleterious Effects of Long-Term Single-chamber Ventricular Pacing in Patients With Sick Sinus Syndrome: The Hidden Benefits of dual-Chamber Pacing," J Am Coll Cardiol. 1992;19:1542-1549.

Klug, Didier MD et al., "Systemic Infection Related to Endocarditis on Pacemaker Leads—Clinical Presentation and Management," Circulation. 1997;95:2098-2107.

Korkeila, Petri et al., "Clinical and laboratory risk factors of thrombotic complications after pacemaker implantation: a prospective study," Europace. 2010;12:817-824.

Marrie, Thomas J. MD et al., "A Scanning and Transmission Electron Microscopic Study of an Infected Endocardial Pacmaker Lead," Circulation. 1982;66(6):1339-1341.

Menozzi, Carlo et al., "Intrapatient Comparison Between Chronic VVIR and DDD pacing in Patients Affected by High Degree AV Block Without Heart Failure," PACE. 1990(Dec-Pt II);13:1816-1822.

Stellbrink, Christoph et al.," Technical considerations in implanting left ventricular pacing leads for cardiac resynchronization therapy," European Heart Journal Supplements. 2004;6(Supp D):D43-D46.

Stickler, J. William PhD, "Totally Self-Contained Intracardiac Pacemaker," J Electrocardiology. 1970;3(3-4):325-331.

Van Rooden, Cornelis J. MD et al., "Incidence and Risk Factors of Early Venous Thrombosis Associated with Permanent Pacemaker Leads," J Cardiovasc Electrophysiol. Nov. 2004;15:1258-1262.

Vardas, P.E. et al., "A Miniature Pacemaker Introduced Intravenously and Implanted Endocardially. Preliminary Findings from an Experimental Study," Eur J Card Pacing Electrophysiol. 1991;1:27-30.

Voet, J.G. et al., "Pacemaker lead infection: report of three cases and review of the literature," Heart. 1999;81:88-91.

Walters, M.I. et al., "Pulmonary Embolization of a Pacing Electrode Fragment Complicating Lead Extraction," PACE. 1999;22:823-824.

* cited by examiner

RIGHT LATERAL VIEW

AP VIEW

SINGLE-CHAMBER LEADLESS INTRA-CARDIAC MEDICAL DEVICE WITH DUAL-CHAMBER FUNCTIONALITY AND SHAPED STABILIZATION INTRA-CARDIAC EXTENSION

CROSS REFERENCE TO RELATED APPLICATIONS

This application relates to and claims priority benefits from U.S. Provisional Application No. 61/555,390, filed Nov. 3, 2011, entitled "Single Chamber Leadless Implantable Medical Device with Dual Chamber Functionality and Shaped Stabilization Appendage," which is hereby incorporated by reference in its entirety. This application also relates to U.S. patent application Ser. No. 13/352,048, filed Jan. 17, 2012, entitled "Single-Chamber Leadless Intra-Cardiac Medical Device with Dual-Chamber Functionality," and Ser. No. 13/352,136, filed Jan. 17, 2012, entitled "Dual-Chamber Leadless Intra-Cardiac Medical Device with Intra-Cardiac Extension," which are hereby incorporated by reference in their entirety.

FIELD OF THE INVENTION

Embodiments of the present invention generally relate to implantable medical devices, and more particularly to leadless intra-cardiac medical devices that afford dual chamber functionality from a position within a single chamber of the heart. As used herein, the term "leadless" generally refers to an absence of electrically-conductive leads that traverse vessels or other anatomy outside of the intra-cardiac space, while "intra-cardiac" means generally, entirely within the heart and associated vessels, such as the SVC, IVC, CS, pulmonary arteries and the like.

BACKGROUND OF THE INVENTION

Current implantable medical devices (IMD) for cardiac applications, such as pacemakers, include a "housing" or "can" and one or more electrically-conductive leads that connect to the can through an electro-mechanical connection. The can is implanted outside of the heart, in the pectoral region of a patient and contains electronics (e.g., a power source, microprocessor, capacitors, etc.) that provide pacemaker functionality. The leads traverse blood vessels between the can and heart chambers in order to position one or more electrodes carried by the leads within the heart, thereby allowing the device electronics to electrically excite or pace cardiac tissue and measure or sense myocardial electrical activity.

To sense atrial cardiac signals and to provide right atrial chamber stimulation therapy, the can is coupled to an implantable right atrial lead including at least one atrial tip electrode that typically is implanted in the patient's right atrial appendage. The right atrial lead may also include an atrial ring electrode to allow bipolar stimulation or sensing in combination with the atrial tip electrode.

Before implantation of the can into a subcutaneous pocket of the patient, however, an external pacing and measuring device known as a pacing system analyzer (PSA) is used to ensure adequate lead placement, maintain basic cardiac functions, and evaluate pacing parameters for an initial programming of the IMD. In other words, a PSA is a system analyzer that is used to test an implantable device, such as an implantable pacemaker.

To sense the left atrial and left ventricular cardiac signals and to provide left-chamber stimulation therapy, the can is coupled to the "coronary sinus" lead designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead is designed to: receive atrial and/or ventricular cardiac signals; deliver left ventricular pacing therapy using at least one left ventricular tip electrode for unipolar configurations or in combination with left ventricular ring electrode for bipolar configurations; deliver left atrial pacing therapy using at least one left atrial ring electrode as well as shocking therapy using at least one left atrial coil electrode.

To sense right atrial and right ventricular cardiac signals and to provide right-chamber stimulation therapy, the can is coupled to an implantable right ventricular lead including a right ventricular (RV) tip electrode, a right ventricular ring electrode, a right ventricular coil electrode, a superior vena cava (SVC) coil electrode, and so on. Typically, the right ventricular lead is inserted transvenously into the heart so as to place the right ventricular tip electrode in the right ventricular apex such that the RV coil electrode is positioned in the right ventricle and the SVC coil electrode will be positioned in the right atrium and/or superior vena cava. Accordingly, the right ventricular lead is capable of receiving cardiac signals, and delivering stimulation in the form of pacing and shock therapy to the right ventricle.

Although a portion of the leads, as well as the IMD itself are outside of the patient's heart. Consequently, bacteria and the like may be introduced into the patient's heart through the leads, as well as the IMD, thereby increasing the risk of infection within the heart. Additionally, because the IMD is outside of the heart, the patient may be susceptible to Twiddler's syndrome, which is a condition caused by the shape and weight of the IMD itself. Twiddler's syndrome is typically characterized by a subconscious, inadvertent, or deliberate rotation of the IMD within the subcutaneous pocket formed in the patient. In one example, a lead may retract and begin to wrap around the IMD. Also, one of the leads may dislodge from the endocardium and cause the IMD to malfunction. Further, in another typical symptom of Twiddler's syndrome, the IMD may stimulate the diaphragm, vagus, or phrenic nerve, pectoral muscles, or brachial plexus. Overall, Twiddler's syndrome may result in sudden cardiac arrest due to conduction disturbances related to the IMD.

In addition to the foregoing complications, leads may experience certain further complications, such as incidences of venous stenosis or thrombosis, device-related endocarditis, lead perforation of the tricuspid valve and concomitant tricuspid stenosis; and lacerations of the right atrium, superior vena cava, and innominate vein or pulmonary embolization of electrode fragments during lead extraction.

To combat the foregoing limitations and complications, small sized devices configured for intra-cardiac implant have been proposed. These devices, termed leadless pacemakers (LLPM) are typically characterized by the following features: they are devoid of leads that pass out of the heart to another component, such as a pacemaker outside of the heart; they include electrodes that are affixed directly to the "can" of the device; the entire device is attached to the heart; and the device is capable of pacing and sensing in the chamber of the heart where it is implanted.

LLPM devices that have been proposed thus far offer limited functional capability. These LLPM devices are able to sense in one chamber and deliver pacing pulses in that same chamber, and thus offer single chamber functionality. For example, an LLPM device that is located in the right atrium would be limited to offering AAI mode functionality. An AAI mode LLPM can only sense in the right atrium, pace in the right atrium and inhibit pacing function when an intrinsic event is detected in the right atrium within a preset time limit. Similarly, an LLPM device that is located in the right ventricle would be limited to offering VVI mode functionality. A VVI mode LLPM can only sense in the right ventricle, pace in the right ventricle and inhibit pacing function when an intrinsic event is detected in the right ventricle within a preset time limit. To gain widespread acceptance by clinicians, it would be highly desired for LLPM devices to have dual chamber pacing/sensing capability (DDD mode) along with other features, such as rate adaptive pacing.

It has been proposed to implant sets of multiple LLPM devices within a single patient, such as one or more LLPM devices located in the right atrium and one or more LLPM devices located in the right ventricle. The atrial LLPM devices and the ventricular LLPM devices wirelessly communicate with one another to convey pacing and sensing information there between to coordinate pacing and sensing operations between the various LLPM devices.

However, these sets of multiple LLPM devices experience various limitations. For example, each of the LLPM devices must expend significant power to maintain the wireless communications links. The wireless communications links should be maintained continuously in order to constantly convey pacing and sensing information between, for example, atrial LLPM device(s) and ventricular LLPM device(s). This pacing and sensing information is necessary to maintain continuous synchronous operation, which in turn draws a large amount of battery power.

Further, it is difficult to maintain a reliable wireless communications link between LLPM devices. The LLPM devices utilize low power transceivers that are located in a constantly changing environment within the associated heart chamber. The transmission characteristics of the environment surrounding the LLPM device change due in part to the continuous cyclical motion of the heart and change in blood volume. Hence, the potential exists that the communications link is broken or intermittent.

SUMMARY OF THE INVENTION

In accordance with one embodiment, a leadless intra-cardiac medical device (LIMD) is provided with dual chamber functionality, without leads, despite the fact that the entire device is located in one chamber. In one embodiment, the LIMD stimulates and senses the right atrium (RA) and right ventricle (RV) chambers, even though it is entirely located in the RA. The electrodes enable delivering stimulus and sensing in different chambers of the heart and thus provide physiological synchronization of myocardial contraction in multiple chambers.

In another embodiment, an LIMD is provided that may be located in the RV, deliver stimulus and sense either the RA or the left ventricle (LV). Alternatively, the LIMD may be located in the RA and configured to electrically stimulate the RV and LV. This last LLPM configuration or placement may be done in a manner such that Hisian or para-Hisian pacing is achieved.

In accordance with an embodiment, a leadless intra-cardiac medical device (LIMD) is provided, comprised of a housing configured to be implanted entirely within a single local chamber of the heart, the local chamber having local wall tissue that constitutes part of a conduction network of the local chamber. A base is provided on the housing, the base configured to be secured to a septum that separates the local chamber from an adjacent chamber, the adjacent chamber having distal wall tissue, with respect to the local chamber that constitutes part of a conduction network of the adjacent chamber. A first electrode is provided at a first position on the base such that, when the device is implanted in the local chamber, the first electrode engages wall tissue at a local activation site within the conduction network of the local chamber. A second electrode is provided at a second position on the base and extending outward such that, when the device is implanted in the local chamber, the second electrode engages wall tissue at a distal activation site within the conduction network of the adjacent chamber. A controller is provided within the housing to cause stimulus pulses to be delivered, in a synchronous manner, through the first and second electrodes to the local and distal activation sites, respectively, such that stimulus pulses delivered at the distal activation site are timed to cause contraction of the adjacent chamber in a predetermined relation to contraction of the local chamber. Optionally, the controller is configured to control delivery of the stimulus pulses from the first and second electrodes in accordance with a DDD pacing mode or a DDDR pacing mode.

The septum may represent a portion of the tricuspid annulus. The base of the housing is configured to engage an activation site on the tricuspid annulus. The second electrode delivers stimulus pulses to the tricuspid annulus to initiate activation in a right ventricle. The controller may be configured to control delivery, from the first and second electrodes, of the stimulus pulses to a right atrium and a right ventricle, while the LIMD is entirely located in one of the right atrium and right ventricle.

The distal wall tissue constitutes wall tissue of at least one of a left atrium, a right ventricle, and a left ventricle. The distal wall tissue is physiologically responsive to distal activation events originating in the at least one of left atrium, right ventricle, and left ventricle.

In accordance with an embodiment, the housing may also include an extension arm having the first electrode located on a distal end thereof. The extension arm may be configured to extend into and engage the local wall tissue in an appendage area of the local chamber. Optionally, the housing may also include an extension arm and a stabilization arm joined to a top end of the housing. The extension arm may have the first electrode located on a distal end thereof to extend into and engage the local wall tissue in an appendage area of the local chamber. The stabilization arm may have a distal end that extends to and engages an opposed stabilization area of the local chamber. The stabilization arm may have a distal end that extends to and engages a superior vena cava of the heart. The extension arm and a stabilization arm may be pivotally joined to a hinge assembly located at a top end of the housing. The extension arm and a stabilization arm may be securely joined to a top end of the housing. The extension arm and stabilization arm may be biased to flare outward away from one another when in a deployed position such that distal ends of the stabilization and extension arms engage the local chamber in opposed areas remote from the base of the housing.

Certain embodiments provide a leadless intra-cardiac medical device configured to be implanted entirely within a heart of a patient. The device may include a housing and a stabilizing intra-cardiac intra-cardiac device extension. The housing is configured to be securely attached to an interior wall portion of a chamber of the heart. The extension is connected to the housing, and is configured to be passively secured within the heart.

The extension may include a loop member. The loop member is configured to be passively secured within one or both of the chamber of the heart or a superior vena cava of the heart. The loop member may include first and second loops connected to one another. Each of the first and second loops may have a perimeter that flares in a lateral direction with respect to a longitudinal axis of the loop body. The loop member may include a perimeter shaped as a disc, oval, circle, tube, rectangle, or triangle.

The loop member may include a plurality of interconnected loops. Each of the plurality of interconnected loops may be commonly aligned and oriented with respect to one another. The plurality of interconnected loops may include a first loop and a second loop. The first loop may be oriented orthogonal to the second loop.

A first of the plurality of interconnected loops may be aligned in a first orientation and a second of the plurality of interconnected loops may be aligned in a second orientation. The first orientation differs from the second orientation so that the first and second of the plurality of interconnected loops are oriented out of plane with one another.

The device may also include at least one electrode secured to the loop member. The electrode is configured to contact tissue within the heart, and provide one or both of sensing or stimulus.

The device may also include at least one radio marker secured to the loop member. The radio marker is configured to allow the LIMD system to be tracked within patient anatomy.

The device may also include an anchoring member extending from a distal end. The anchoring member is configured to securely anchor the housing to tissue within the heart. The anchoring member may include a securing helix. The securing helix may serve as an electrode.

In an embodiment, the stabilizing intra-cardiac device extension may include a first curved portion with respect to the housing. The first curved portion may be connected to a first linear region that connects to a second curved portion. The first curved portion may be approximately 90 degrees with respect to the housing. The second curved portion may be approximately 180 degrees away from the housing. The second curved portion may connect to a second linear region that connects to a third curved portion. The second curved portion may be configured to be implanted within a right atrial appendage of the heart. An electrode may be located proximate a junction of the second curved portion and the second linear region. The third curved portion may form an extending arc that approximates a 90 degree turn away from the housing that terminates at a tail end.

Certain embodiments provide a method of implanting a leadless intra-cardiac medical device (LIMD) entirely within a heart of a patient. The device includes a housing and a stabilizing intra-cardiac device extension connected to the housing. The method may include navigating the device into the heart with an introducer assembly, the extension held in a collapsed installation shape within the introducer assembly, positioning the introducer assembly so that the housing is proximate an implant site within the heart, securely anchoring the housing to the implant site, separating the introducer assembly and the device, thereby allowing the extension to expand to a deployed implanted shape, and securing the extension within a portion of the heart so that the device is entirely within the heart of the patient.

In accordance with embodiments herein, the stabilizing intra-cardiac device extension comprises an elongated body, and expanding includes permitting the elongated body to expand to a pre-loaded shape in which a first curved segment bends at an angle with respect to a longitudinal axis of the housing, wherein the first curved segment merges into a first linear region that extends laterally from the housing toward a tissue of interest, the elongated body including an electrode provided thereon at a position configured to contact the tissue of interest.

In accordance with optional embodiments herein, the stabilizing intra-cardiac device extension comprises an elongated body, and expanding includes permitting the elongated body to expand to a pre-loaded shape such that a first linear region extends laterally from the housing, along a lateral axis, and merges with a second curved segment, the second curved segment turning at an angle with respect to a longitudinal axis of the housing and a lateral axis of the first linear region.

In accordance with other embodiments herein, the stabilizing intra-cardiac device extension comprises an elongated body, and expanding includes permitting the elongated body to expand to a pre-loaded shape in which first and second linear regions are joined to one another through a curved segment, the method further comprising positioning the first linear region and the curved segment to extend into a right atrial appendage, and positioning the second linear region to extend from the right atrial appendage toward the SVC.

In accordance with embodiments herein, the extension comprises an elongated body that includes first and second curved segments joined to one another by a linear region, at least one of the first and second curved segments including an electrode, the method further comprising positioning the electrode to contact tissue of interest.

In accordance with embodiments herein, the extension comprises an elongated body that is tubular in shape and includes a metal braid, the method further comprising applying at least one of rotational and longitudinal pressure upon the IC device extension, the braid resisting rotational torque and longitudinal compression to facilitate delivery of rotational forces and longitudinal pressure to the housing of the device.

Optionally, the method may comprise guiding the extension to engage a first region of the heart, the first region representing at least one of a superior vena cava, an inferior vena cava, a coronary sinus, and a pulmonary artery. Optionally, the extension may include a stabilizer end-segment that is pre-formed to bend at an angle and fit against an interior of at least one of a superior vena cava, an inferior vena cava, a coronary sinus, and a pulmonary artery.

In accordance with embodiments herein, the method may comprising configuring a controller of the device to control delivery of stimulus pulses from first and second electrodes in accordance with a DDD pacing mode to a right atrium and right ventricle, while the device is entirely located in one of the right atrium and right ventricle.

BRIEF DESCRIPTION OF THE DRAWINGS

FIG. 4A illustrates a LIMD that has a base with spikes extending there from.

DETAILED DESCRIPTION

Figure 1:
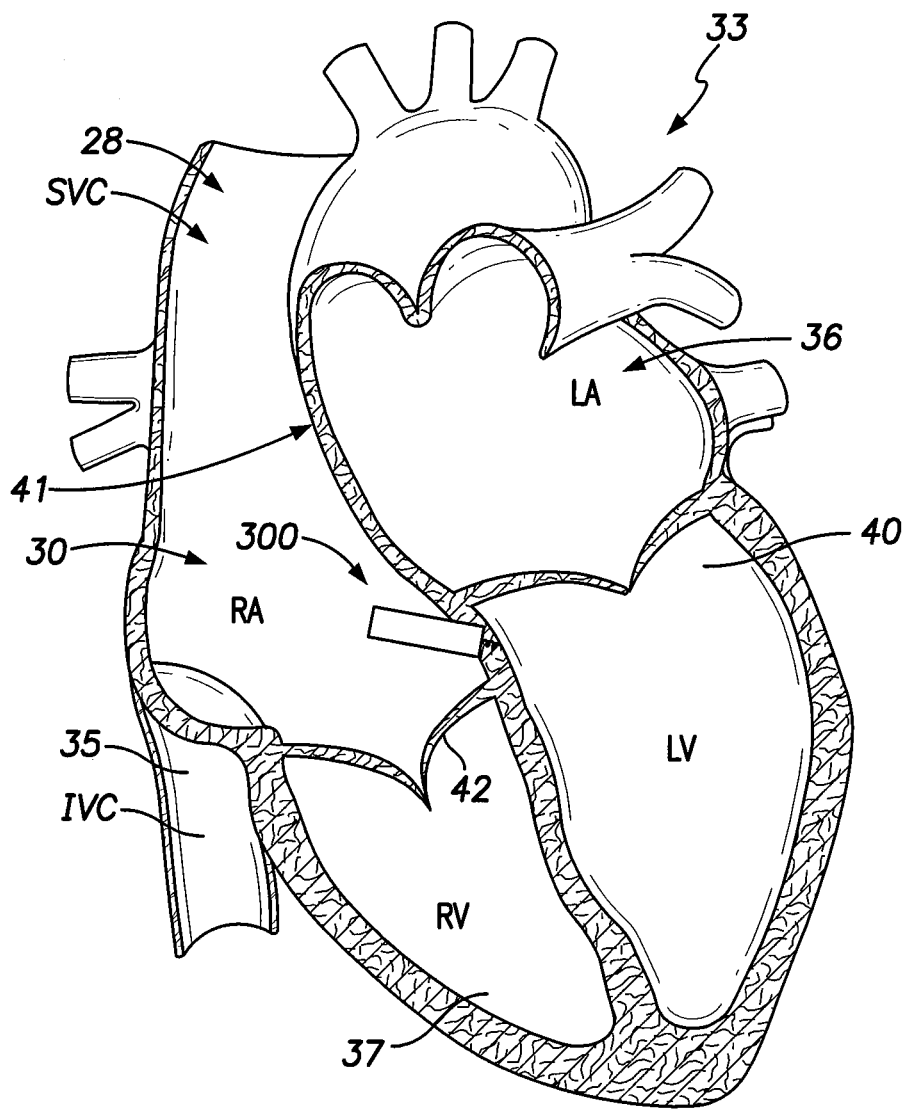
FIG. 1 illustrates a sectional view of a patient's heart with a leadless intra-cardiac medical device (LIMD) implanted therein.

Dual-chamber permanent pacemakers (PPM), operating in the DDD or DDDR mode, are indicated for patients with complete atrioventricular (AV) block, sick sinus syndrome, and paroxysmal AV block. The use of DDD or DDDR mode PPMs in patients with a high degree of AV block is shown to improve subjective metrics of patient life and increase peak velocity and cardiac output, compared to VVIR PPMs. Additionally, another study demonstrates reduced incidence of atrial fibrillation (AF) and increased patient longevity in patients with sick sinus syndrome after the time of DDDR PPM implant. These significant benefits, accrued to the three previously-described subgroups of implant patients, provide a strong impetus for using DDDR PPMs in those recipients.

The benefits of conventional DDD or DDDR PPMs are counterbalanced by the increased risk of complications with the additional lead necessary for these PPMs (compared to single-chamber devices). A preferred solution to this dilemma offered by embodiments herein eliminate the need to use leads by providing an LIMD with DDDR mode functionality. As a result, patients suffering from various degrees of AV block or sick sinus syndrome may receive dual-chamber pacing therapy without an increased risk of complications (such as lead-associated infections caused by biofilm formation 14 or explant-related difficulties). In particular, decreased incidence of device-related infections may be achieved by a DDDR mode-capable LIMD as a result of the device body's small surface area (compared to conventional PPMs and leads), which presents a reduced substrate for bacterial or fungal adhesion.

Myocardial contraction results from a change in voltage across the cell membrane (depolarization), which leads to an action potential. Although contraction may happen spontaneously, it is normally in response to an electrical impulse. In normal physiologic behavior, this impulse starts in the sino-atrial (SA) node where a collection of cells are located at the junction of the right atrium and superior vena cava. These specialized cells depolarize spontaneously, and cause a wave of contraction to follow a conduction network along the tissue wall of the atria. Following atrium contraction, the impulse is delayed at the atrio-ventricular (AV) node, located in the septum wall of the right atrium. From here HIS-Purkinje fibers allow rapid conduction of the electrical impulse to propagate along the conduction network formed by the right and left branches in the RV and LV tissue walls, causing almost simultaneous depolarization of both ventricles, approximately 0.2 seconds after the initial impulse has arisen in the sino-atrial node. Depolarization of the myocardial cell membrane causes a large increase in the concentration of calcium within the cell, which in turn causes contraction by a temporary binding between two proteins, actin and myosin. The cardiac action potential is much longer than that of skeletal muscle, and during this time the myocardial cell is unresponsive to further excitation. Hence, in a general sense, the tissue walls of each chamber constitute part of a conduction network of the corresponding chamber.

FIG. 1 provides a sectional view of a patient's heart 33 and shows a leadless intra-cardiac medical device 300. The leadless implantable medical device 300 has been placed through the superior vena cava 28 into the right atrium 30 of the heart 33. FIG. 1 also shows the inferior vena cava 35, the left atrium 36, the right ventricle 37, the left ventricle 40, the atrial septum 41 that divides the two atria 30, 36, the ventricular vestibule VV, the right atrial appendage (RAA), and the tricuspid valve 42 between the right atrium 30 and right ventricle 37. The reader will appreciate that the view of FIG. 1 is simplified and somewhat schematic, but that nevertheless FIG. 1 and the other views included herein will suffice to illustrate adequately the placement and operation of embodiments of the present invention. The term "septum" shall be used throughout to generally refer to any portion of the heart separating two chambers (e.g. RA to LA, RV to LV). The leadless implantable medical device (LIMD) 300 is formed in accordance with an embodiment. The LIMD 300 may represent a pacemaker that functions in a DDD mode or a DDDR-mode, a cardiac resynchronization device, a cardioverter, a defibrillator and the like. When in DDD or DDDR-mode, the LIMD 300 may sense in two chambers, pace in two chambers and inhibit pacing in either chamber based on intrinsic events sensed in that chamber or in the other chamber. The LIMD 300 comprises a housing configured to be implanted entirely within a single local chamber of the heart. For example, the LIMD 300 may be implanted entirely and solely within the right atrium or entirely and solely within the right ventricle. Optionally, the LIMD 300 may be implanted entirely and solely within the left atrium or left ventricle through more invasive implant methods.

For convenience, hereafter the chamber in which the LIMD 300 is implanted shall be referred to as the "local" chamber. The local chamber includes a local chamber wall that is physiologically response to local activation events originating in the local chamber. The local chamber is at least partially surrounded by local wall tissue that forms or constitutes at least part of a conduction network for the associated chamber. For example, during normal operation, the wall tissue of the right atrium contracts in response to an intrinsic local activation event that originates at the sinoatrial (SA) node and in response to conduction that propagates along the atrial wall tissue. For example, tissue of the right atrium chamber wall in a healthy heart follows a conduction pattern, through depolarization, that originates at the SA node and moves downward about the right atrium until reaching the atria ventricular (AV) node. The conduction pattern moves along the chamber wall as the right atrium wall contracts.

The term "adjacent" chamber shall refer to any chamber separated from the local chamber by tissue (e.g., the RV, LV and LA are adjacent chambers to the RA; the RA and LV are adjacent chambers to the LA; the RA and RV are adjacent to one another; the RV and LV are adjacent to one another, and the LV and LA are adjacent to one another).

The local chamber (e.g., the right atrium) has various tissue of interest, such as a septum, that separate the local chamber from the adjacent chambers (e.g., right ventricle, left atrium, left ventricle). In certain portions or segments of the septum, segments of the septum, behave in physiologically different manners. For example, in certain segments of the septum for the right atrium, even during normal healthy operation, the septum wall tissue does not propagate the conduction in the same manner or pattern as in a majority of the wall tissue of the right atrium wall. For example, septum wall tissue in the right atrium, referred to as the ventricular vestibule tissue, does not behave physiologically in the same manner as the non-septum atrial wall tissue. Instead, the right ventricular vestibule tissue is physiologically coupled to the wall tissue in the right ventricle and in accordance therewith exhibits a conduction pattern that follows the conduction pattern of the right ventricular wall tissue. The right ventricular vestibule tissue is one example of a septum segment that partially separates a local chamber (e.g., the right atrium) from an adjacent chamber (e.g., right ventricle), yet is physiologically coupled to conduction in the adjacent chamber (e.g., right ventricle).

In the example of FIG. 1, the LIMD 300 is implanted in an area near different regions of tissue that follow the conductive pattern of different chambers of the heart. Optionally, the LIMD 300 may be implanted such that at least one electrode on the base of the LIMD 300 engages tissue that is part of the conductive network of the one chamber, while at least one other electrode projects from the base into tissue that is part of the conductive network of another chamber. For example, when the LIMD 300 may be implanted within or near the triangle of Koch in an area adjacent the ventricular vestibule. The conductive network of the tissue in the ventricular vestibule follows the conductive pattern of the right ventricle. Therefore, the LIMD 300 may be implanted near the edge of the triangle of Koch such that one or more proximal electrodes, extending from the LIMD 300, are electrically coupled to the conductive network of the right atrium, while one or more other distal electrodes, extend diagonally to become electrically coupled to the conductive network of the right ventricle (e.g., the ventricular vestibule). Optionally, the LIMD 300 may be positioned with the base located against the RA wall above the mitral valve, but with a distal electrode that projects into the septum to ventricular tissue of the right or left ventricle.

Figure 3A:
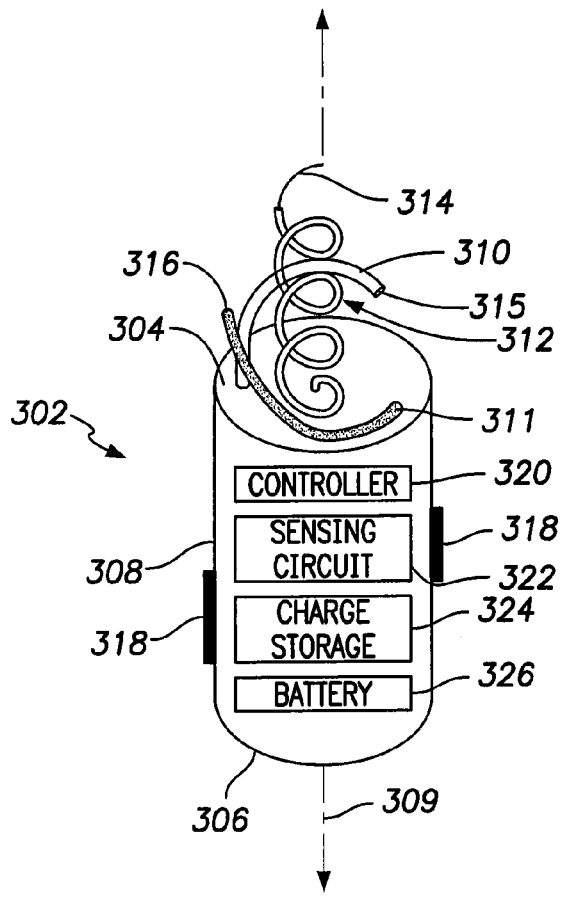
FIG. 3A illustrates a side perspective view of the LIMD of FIG. 1 oriented with the base facing upward to illustrate electrodes in more detail.
Figure 3B:
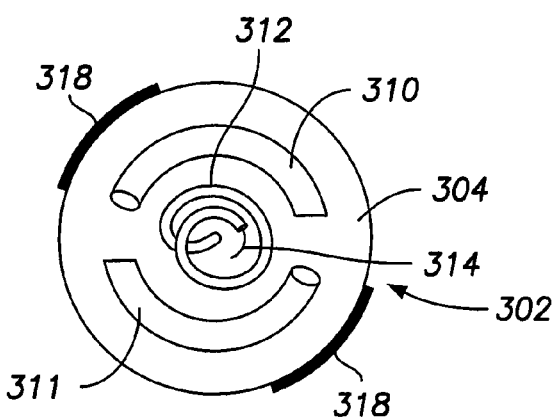
FIG. 3B illustrates a bottom plan view of the LIMD of FIG. 3A.

FIGS. 3A and 3B illustrate the LIMD 300 in more detail. FIG. 3A illustrates a side perspective view of the LIMD 300 of FIG. 1 oriented with the base 304 facing upward to illustrate electrodes 310-312 in more detail. FIG. 3B illustrates a bottom plan view of the LIMD 300. The LIMD 300 comprises a housing 302 having a proximal base 304, a distal top end 306, and an intermediate shell 308 extending between the proximal base 304 and the distal top end 306. The shell 308 is elongated and tubular in shape and extends along a longitudinal axis 309.

The base 304 includes one or more electrodes 310-312 securely affixed thereto and projected outward. For example, the outer electrodes 310, 311 may be formed as large semi-circular spikes or large gauge wires that wrap only partially about the inner electrode 312. The electrodes 310, 311 may be located on opposite sides of, and wound in a common direction with, the inner electrode 312. The first or outer electrodes 310, 311 are provided directly on the housing 302 of the LIMD 300 at a first position, namely at or proximate a periphery of the base 304 of the housing. The outer electrodes 310, 311 are positioned near the periphery of the base 304 such that, when the LIMD 300 is implanted in the local chamber (e.g., right atrium), the outer electrodes 310, 311 engage the local chamber wall tissue at tissue of interest for a local activation site that is near the surface of the wall tissue, and that is within the conduction network of the local chamber. The outer electrodes 310, 311 are physically separated or bifurcated from one another and have separate distal outer tips 315, 316. The outer electrodes 310, 311 are electrically joined to one another (i.e., common), but are electrically separated from the inner electrode 312.

The second or inner electrode 312 is also provided directly on the housing 302 of the LIMD 300 at a second position, namely at or proximate to a central portion of the base 304 of the housing. The inner electrode 312 is positioned near the center of the base 304 and is elongated such that, when the LIMD 300 is implanted in the local chamber, the inner electrode 312 extends a majority of the way through the wall tissue (e.g. septum) until reaching tissue of interest near the adjacent chamber wall. The inner electrode 312 is inserted to a depth such that a distal tip thereof is located at tissue of interest for an activation site that is physiologically coupled to wall tissue of the adjacent chamber (e.g. right ventricle). For example, the inner electrode 312 may extend until the distal tip extends at least partially through a septum to a position proximate to a distal wall tissue within the conduction network of the adjacent chamber. Optionally, the inner electrode 312 may be inserted at a desired angle until the distal end enters the ventricular vestibule. By located the distal tip of the inner electrode 312 at an adjacent chamber activation site, the inner electrode 312 initiates contraction at a distal activation site within the conduction network of the adjacent chamber without physically locating the LIMD 300 in the adjacent chamber. The inner and outer electrodes 310-312 may be formed as multiple cathode electrodes that are actively fixated to the myocardium. The outer cathode electrodes 310, 311 may be configured as screws with a large pitch (e.g. length between adjacent turns), large diameter and may have a length that is relatively short, while the inner electrode 312 is configured as a screw with a common or smaller pitch, small diameter and longer length. The screw shape of the outer electrodes 310, 311 is used to firmly adhere them to the cardiac tissue. The outer electrodes 310, 311 may have very little or no insulation material thereon to facilitate a good electrical connection to local wall tissue along the majority or the entire length of the outer electrodes 310, 311 for delivering stimulus pulses and sensing electrical activity in the local chamber where the LIMD 300 is located.

The inner electrode 312 is shaped in a helix or screw and is longer (e.g., extends a greater distance from the base) than the outer electrodes 310, 311. The inner electrode 312 is fashioned to an appropriate length that permits it to drill a predetermined distance into, or entirely through, the septum at the desired location. For example, the inner electrode 312 may be provided with a desired length sufficient to extend through, or to a desired distance into, a septum region separating two chambers of the heart. For example, the outer electrodes 310, 311 may contact atrial wall tissue within the triangle of Koch, while the inner electrode 312 extends diagonally along the septum into the ventricular vestibule.

The inner electrode 312 may be formed as a single conductive wire or a bundle of conductive wires, where a proximal portion of the wire is covered with insulation, while the distal tip 314 is covered with insulation and is exposed. By covering the proximal portion of the electrode 312 with insulation, this limits electrical conduction of the conductive wire to tissue surrounding the distal tip 314. When implanted, the distal tip 314 of the electrode is located far below the surface tissue of the chamber wall in which the LIMD 300 is located. As a consequence, the distal tip 314 of the inner electrode 312 directly engages or is located proximate to the surface tissue of an adjacent chamber wall. Hence, the distal tip will 314 senses electrical activity from the conductive network of the adjacent chamber that is representative of physiologic behavior (e.g., conduction pattern) of the adjacent chamber. Also, when delivering stimulus pulses, the distal tip 314 will deliver the pulses into the conductive network of the adjacent chamber wall.

The combination of the inner and outer screw type electrodes 310-312 also imparts extra mechanical stability to the LIMD 300, preventing unwanted torque and shear effects as the heart wall moves during contraction. Otherwise, such effects would otherwise predispose the LIMD 300 to dislodgement. Extraction could simply entail a combination of unscrewing of the two cathodes in conjunction with a slight tugging force directed away from the myocardial wall.

Optionally, a single anode electrode or multiple anode electrodes 318 may be provided. The anode electrode(s) 318 may be located along one or more sides of the shell 308, and/or on the top end 306 of the LIMD 300.

The LIMD 300 includes a charge storage unit 324 and sensing circuit 322 within the housing 302. The sensing circuit 322 senses intrinsic activity, while the change storage unit 324 stores high or low energy amounts to be delivered in one or more stimulus pulses. The electrodes 310-312 may be used to deliver lower energy or high energy stimulus, such as pacing pulses, cardioverter pulse trains, defibrillation shocks and the like. The electrodes 310-312 may also be used to sense electrical activity, such as physiologic and pathologic behavior and events and provide sensed signals to the sensing circuit 322. The electrodes 310-312 are configured to be joined to an energy source, such as a charge storage unit 324. The electrodes 310-312 receive stimulus pulse(s) from the charge storage unit 324. The electrodes 310-312 may be the same or different size. The electrodes 310-312 are configured to deliver high or low energy stimulus pulses to the myocardium.

The LIMD 300 includes a controller 320, within the housing 302 to cause the charge storage unit 324 to deliver activation pulses through each of the electrodes 310-312 in a synchronous manner, based on information from the sensing circuit 322, such that activation pulses delivered from the inner electrode 312 are timed to initiate activation in the adjacent chamber. The stimulus pulses are delivered synchronously to local and distal activation sites in the local and distal conduction networks such that stimulus pulses delivered at the distal activation site are timed to cause contraction of the adjacent chamber in a predetermined relation to contraction of the local chamber. The inner and outer electrodes 310-312 are spaced radially and longitudinally apart from one another such that the local activation site (e.g., right atrium) and the distal activation side in the adjacent chamber (e.g., right ventricle) are sufficiently remote from one another within the heart's conductive network to initiate activation in different branches of the hearts conductive network in a time relation that corresponds to the normal hemodynamic timers (e.g. AV delay).

Figure 2:
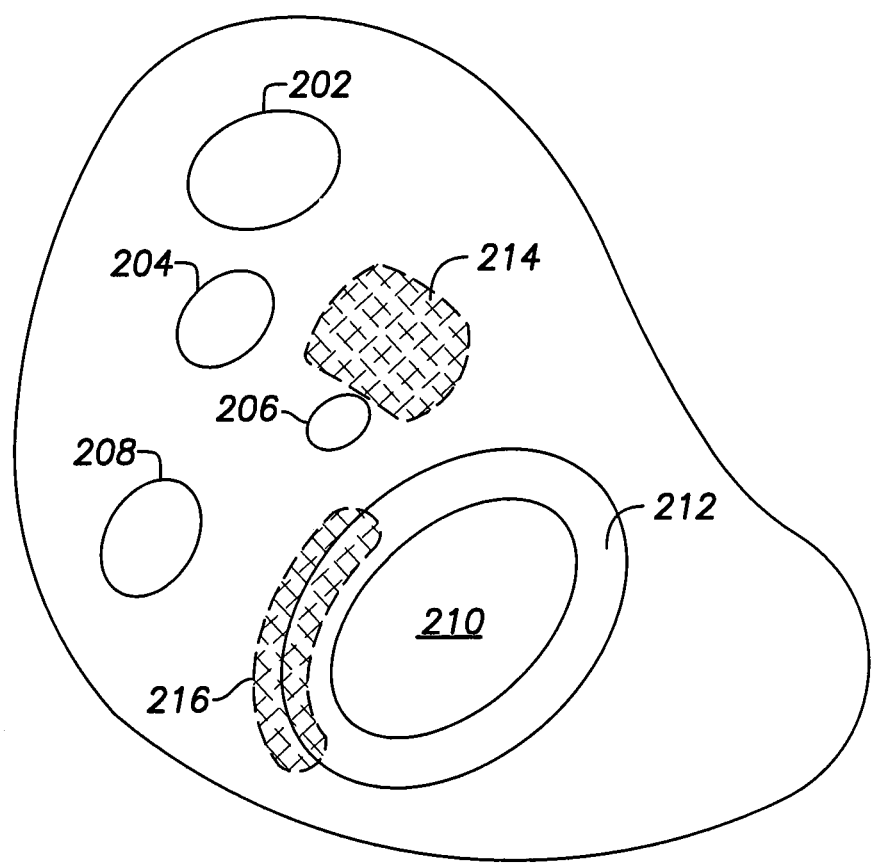
FIG. 2 illustrates a right anterior oblique view representing the interior surface of the right atrium wall.

FIG. 2 illustrates a right anterior oblique view representing the interior surface of the right atrium wall. As shown in FIG. 2, the right atrium wall includes the superior vena cava (SVC) inlet 202, the fosa ovalis 204, coronary sinus 206, IVC 208, tricuspid valve 210 and tricuspid annulus 212 that surrounds the tricuspid valve 210. The LIMD 300 may be implanted in various locations within the RA. For example, the LIMD 300 may be implanted in region 214 which is located immediately adjacent the coronary sinus 206. Region 214 may be contained within the Triangle of Koch. For example, the LIMD 300 may be implanted in region 216 which may represent the ventricular vestibule in an area located adjacent the tricuspid valve 210 along a segment of the tricuspid annulus 212. Region 214 represents a local activation site in the local chamber wall at which contractions may be initiated when stimulus pulses are delivered to the surface tissue in the region 214. Region 216 constitutes a distal activation site at which contractions may be initiated in the right ventricle when stimulus pulses are delivered in the region 216.

The controller 320 may operate the LIMD 300 in various modes, such as in select pacemaker modes, select cardiac resynchronization therapy modes, a cardioversion mode, a defibrillation mode and the like. For example, a typical pacing mode may include DDIR, R, DDOR and the like, where the first letter indicates the chamber(s) paced (e.g., A: Atrial pacing; V: Ventricular pacing; and D: Dual-chamber (atrial and ventricular) pacing). The second letter indicates the chamber in which electrical activity is sensed (e.g., A, V, or D). The code O is used when pacemaker discharge is not dependent on sensing electrical activity. The third letter refers to the response to a sensed electric signal (e.g., T: Triggering of pacing function; I: Inhibition of pacing function; D: Dual response (i.e., any spontaneous atrial and ventricular activity will inhibit atrial and ventricular pacing and lone atrial activity will trigger a paced ventricular response) and O: No response to an underlying electric signal (usually related to the absence of associated sensing function)). The fourth letter indicates rate responsive if R is present.

As one example, the controller 320 may be configured with DDI, DDO, DDD or DDDR mode-capable and the LIMD 300 would be placed in the RA. The screw type electrodes 310, 311 are used to secure it in conductive branch region 214 (FIG. 2). Conductive branch region 214 is contained within the Triangle of Koch and is characterized by more ready activation of RA tissue compared to conductive branch region 216. When the LIMD 300 is secured in conductive branch region 216, it is possible to achieve Hisian/para-Hisian pacing from the RA and perform biventricular stimulation that is more consistent with normal physiology. It may be possible to also perform AV pacing from conductive branch region 216.

As one example, the conductive branch region 216 represents the adjacent chamber activation site within the ventricular vestibule. The inner electrode 312 delivers stimulus pulses to the ventricular vestibule to initiate activation in the right ventricle 37 of the heart. When the LIMD 300 is secured in the conductive branch region septum 216, the inner electrode 312 is located in a minor tissue portion that is non-responsive to the local events and local conduction occurring in the right atrium. The distal end 314 of the inner electrode 312 electrically engages the minor tissue portion that is responsive to non-local events and non-local conduction originating in another chamber.

The sensing circuit 322 receives sensed signals from one or more of the electrodes 310-312. The sensing circuit 322 discriminates between sensed signals that originate in the near field and in the far field. For example, the electrodes 310-311 sense electrical potential across small areas and thereby allow the sensing circuit 322 to discriminate between different sources of electrical signals. In one embodiment, the electrode spacing between electrodes 310, 311 is limited or minimized in order to achieve a select type of sensing such as bipolar sensing which limits or minimizes sensing of far field signals. For example, the electrode 310 may operate as an anode electrode and the electrode 311 may operate as a cathode electrode with a small separation there between such that when far field signals (e.g., signals from the right ventricle) reach the first and second electrodes these far field signals are sensed as a common mode signal with no or a very small potential difference between the electrodes.

In another example, an electrode 312 may be provided with a pair of electrically separate sensing regions thereon. The sensing regions may operate as an anode and as a cathode electrode with a small separation there between such that when far field signals (e.g., signals from the right atrium) reach the first and second sensing regions these far field signals are sensed as a common mode signal with no or a very small potential difference between the sensing regions.

The housing 302 also include a battery 326 that supplies power to the electronics and energy to the change storage unit 324.

Figure 3C:
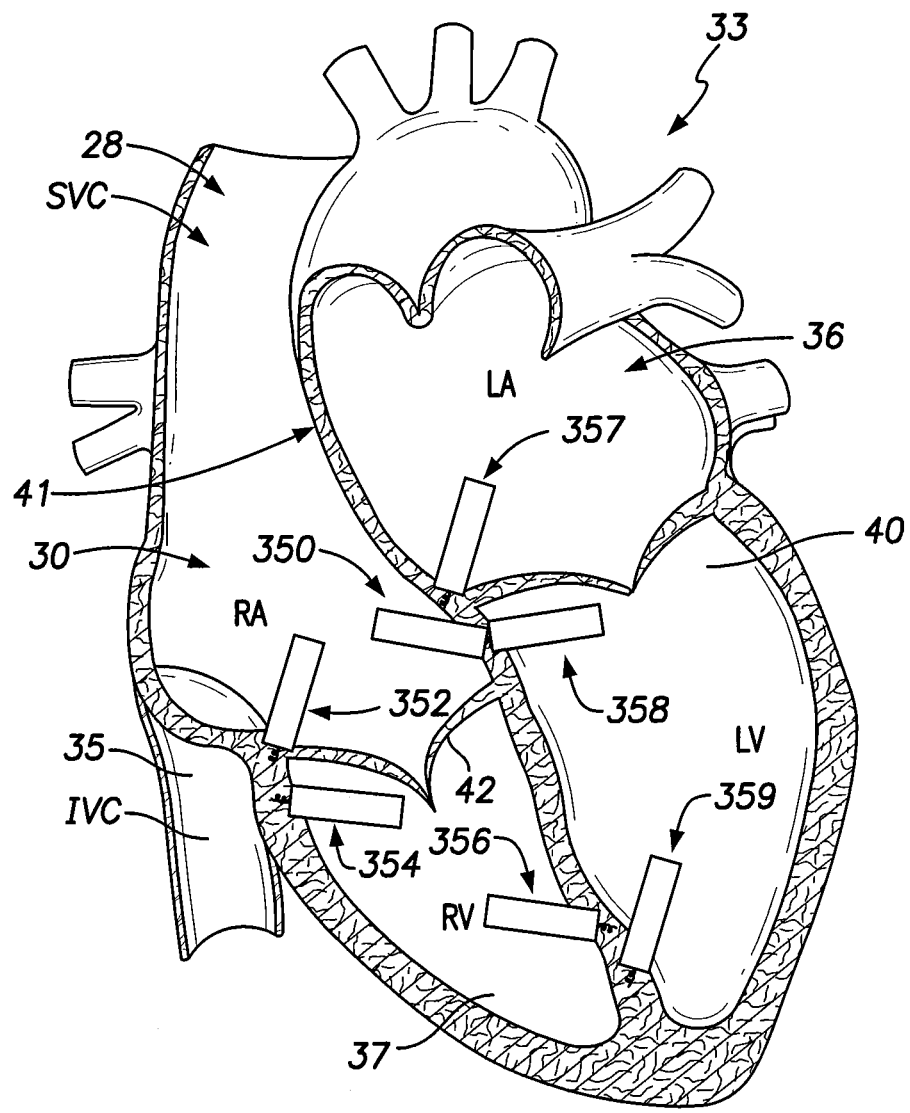
FIG. 3C illustrates examples of locations where an LIMD may be implanted.

FIG. 3C illustrates some of these possible configurations, namely at 350-356. The previous examples involve an LIMD implanted in the RA and capable of pacing the RV. Optionally, the LIMD may also be located in other locations. At 350, the LIMD is capable of HISian or para-HISian pacing to produce excitation of the RV and LV. When the LIMD is implanted at 352, the LIMD is able to provide RA/RV sensing and pacing from the RA. When the LIMD is implanted at 354, the LIMD is able to provide RA/RV sensing and pacing from the RV. When the LIMD is implanted at 356, the LIMD is able to provide RV/LV sensing and pacing from the RV. The LIMDs 357, 358, 359 afford LA/RA pacing and sensing, LV/RA pacing and sensing, and LV/RV pacing and sensing, respectively. These implementations produce excitation of the RV and LV in a manner more consistent with normal physiological function.

Figure 4A:
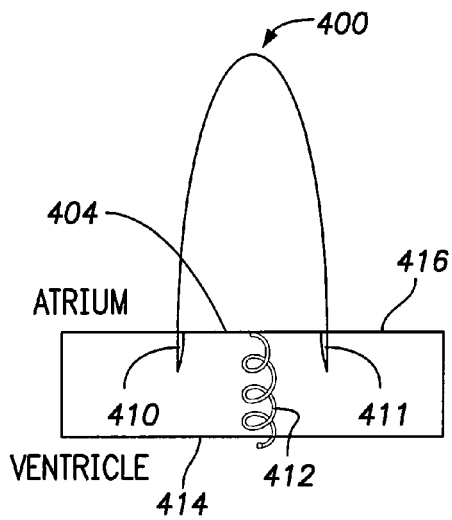

FIGS. 4A-4G illustrate various embodiments of fixation mechanisms that may be used with an LIMD 400. FIG. 4A illustrates a LIMD 400 that has a base 404 with spikes 410, 411 as cathode electrodes extending there from. The spikes 410, 411 are used to fixate the LIMD 400, as well as to deliver stimulus pulses and sense in the local chamber 416 (e.g. atrium). The LIMD 400 also includes an elongated cathode electrode 412 that is used for delivering stimulus pulses and for sensing electrical activity in the conduction network of the adjacent chamber 414 (e.g., the ventricle). The electrode 412 extends entirely through the chamber wall into the adjacent chamber 414. Optionally, the electrode 412 may extend near or up to, but not penetrate the wall tissue into the adjacent chamber 414.

Figure 4B:
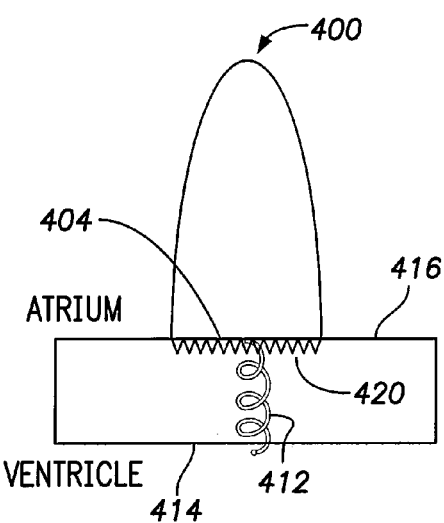
FIG. 4B illustrates a LIMD that has a base with serrated edges that project outward from the base.

FIG. 4B illustrates an LIMD 400 that has a base 404 with an electrode formed as serrated edges 420 that project outward from the base 404. The serrated edges 420 form a skirt encircling the base 404. The serrated edges 420 are electrically active and can be used for delivering stimulus pulses and for sensing conductive activity in the local chamber 416 as well as fixation. The LIMD 400 also includes an elongated cathode electrode 412 that is used for delivering stimulus pulses and for sensing conductive activity in the adjacent chamber 414 (e.g., the ventricle).

Figure 4C:
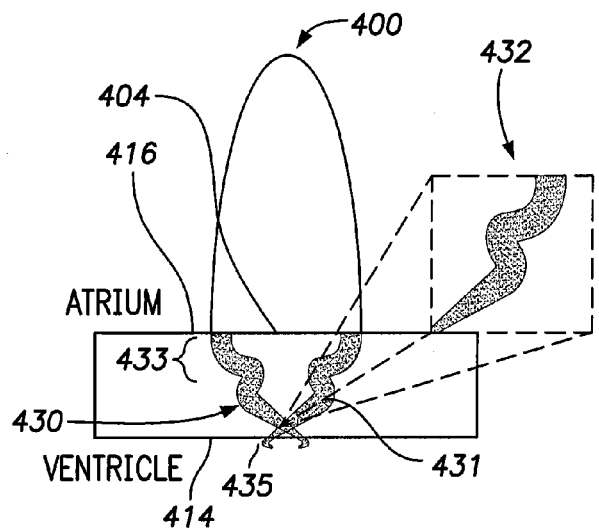
FIG. 4C illustrates a LIMD that has a base with a fixation mechanism similar to a pair of large diameter double-helix, but with a positive deflection near the base.

FIG. 4C illustrates an LIMD 400 that has a base 404 with electrodes formed as a fixation mechanisms 430, 431 similar to a pair of large diameter double-helix, but with a positive deflection 432 near the base 404. The purpose of this shape is to ease in the LIMD 400 during implant, but rendering unscrewing of the LIMD 400 very difficult due to its firm adhering to the wall. There may also be a single helix that varies in diameter or pitch from the proximal end to the distal end, which ensures ease of insertion at implant but causes detachment to be more difficult as tissue conforms to the helix's shape. The fixation mechanism 430 enclosed in insulation except for a proximal region 433 that is exposed and is electrically active in a proximal region near the base 404 in order to deliver stimulus pulses and to sense conductive activity in the local chamber 416. The fixation mechanism 431 is covered in insulation except for a distal region 435 that is exposed and is electrically active near the distal end remote from the base 404 in order to deliver stimulus pulses and to sense conductive activity in the adjacent chamber 414 (e.g., the ventricle).

Figure 4D:
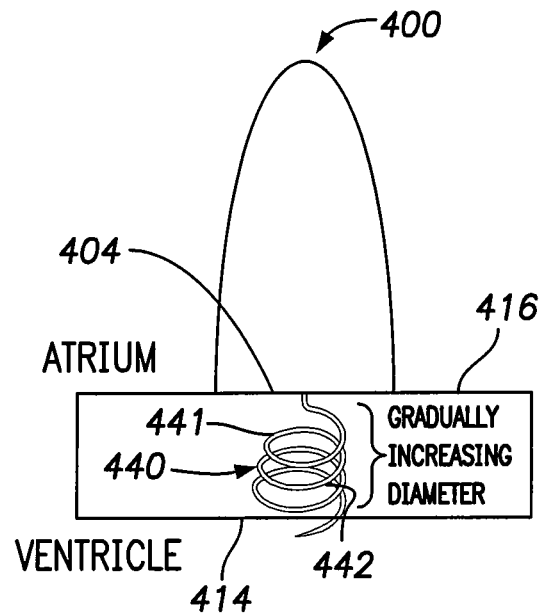
FIG. 4D illustrates a LIMD that has a base with a fixation mechanism that has a screw wire with different thickness at the proximal and distal ends.

FIG. 4D illustrates an LIMD 400 that has a base 404 with a fixation mechanism 440 that has a screw non-circular shape with different cross-sectional thicknesses at the proximal and distal ends 441, 442. By varying the cross sectional thickness at different locations along the fixation mechanism 440, this will afford better fixation of the LIMD 400. The cross-section may gradually increase or step-wise increase along the length of the mechanism 440 with greater distance from the base 404. For example, the fixation mechanism 440 may exhibit progressively widening cross-section toward the distal end 442 to afford better fixation.

Figure 4E:
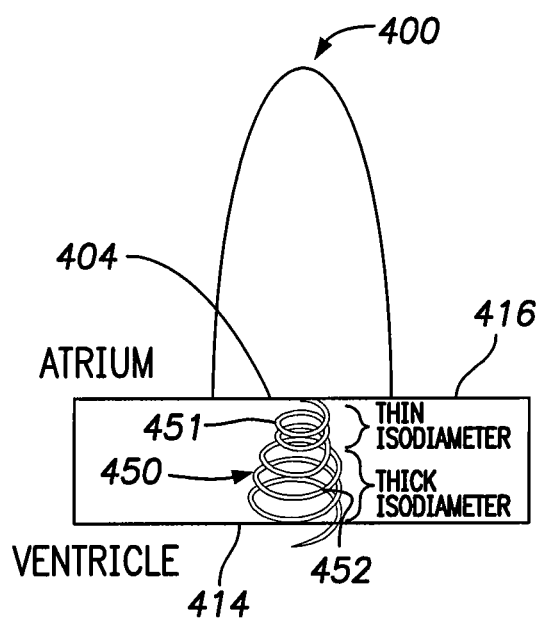
FIG. 4E illustrates a LIMD that has a base with a fixation mechanism that has a screw wire with different diameter at the proximal and distal ends.

FIG. 4E illustrates an LIMD 400 that has a base 404 with a fixation mechanism 450 that has a screw wire shape with different circular diameter at the proximal and distal ends 451, 452. By varying the wire diameter at different locations along the fixation mechanism 450, this will afford better fixation of the LIMD 400. The diameter of the wire may gradually increase or step-wise increase along the length of the mechanism 450 with greater distance from the base 404. The fixation mechanism 450 is formed with two isodiametric sections at the proximal and distal ends 451, 452 which are used to secure the LIMD 400. For example, the proximal end 451 may be thinner in diameter, while the distal end 452 is thicker in diameter.

Figure 4F:
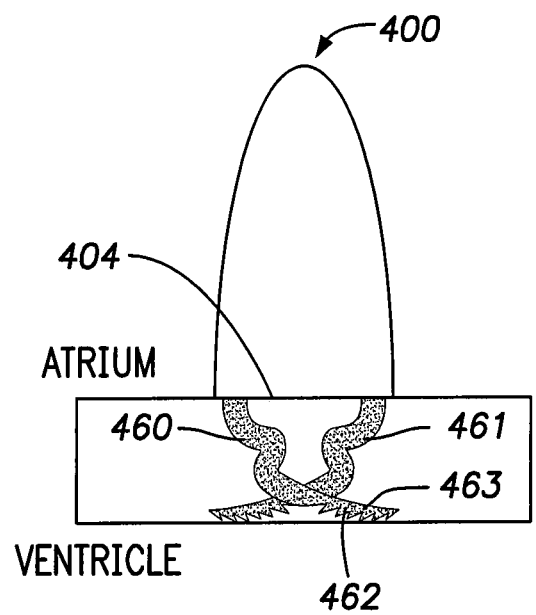
FIG. 4F illustrates a LIMD with a variation in the fixation mechanism shown in FIG. 4C.

FIG. 4F illustrates an LIMD 400 with a variation in the fixation mechanism 430, 431 shown in FIG. 4C. In FIG. 4F, the LIMD 400 includes fixation mechanisms 460, 461 with the distal ends 463 of the large double-helices having serrated edges 462 that prevent the LIMD 400 from unscrewing out of the heart chamber wall.

Figure 4G:
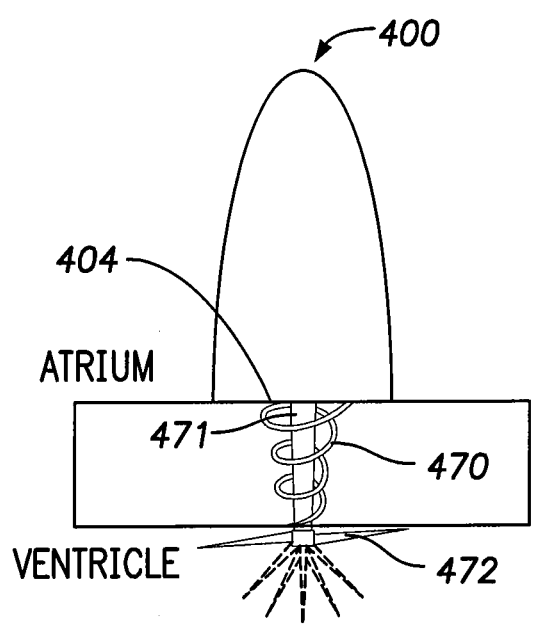
FIG. 4G illustrates a LIMD with a helical cathode electrode that surrounds a long spike electrode.

FIG. 4G illustrates an LIMD 400 with a helical cathode electrode 470 that surrounds a long spike electrode 471. Once implanted, the spike electrode 471 deploys a small mesh 472 similar in shape to an umbrella. The mesh 472 helps secure the LIMD 400 on both ends of the chamber wall.

Optionally, the LIMD 400 may have a single helical active-fixation mechanism that contains one or more passive electrodes on the LIMD 400 body that remain in the heart chamber where the LIMD 400 is implanted. The electrode could be brought into contact with the myocardium when the fixation is engaged. The electrodes shown in FIGS. 4A-4G may be cathodes, anodes or one of each. Optionally, an anode or cathode may be provided on the housing of the LIMD 400.

Next alternative embodiments are described in connection with FIGS. 5A to 7B and FIGS. 9A to 14, in which the LIMD includes an intra-cardiac (IC) device extension. In the embodiments of FIGS. 5A to 7B, the IC device extension includes one or both of at least two portions, namely a stabilization arm and an appendage arm. In the embodiments of FIGS. 9A to 14, the IC device extension is formed as a single elongated body that includes multiple linear regions and curved segments. The elongated body of the IC device extension may have various cross-sectional shapes, such as disc-shaped, oval, circular, tubular, rectangular, square, polygonal, triangular, and the like. Optionally, the IC device extension may have a cross-sectional shape that is paddle shaped or flat, semi-circular, donut shaped and the like. The IC device extensions in the embodiments described herein may be formed from silicon alone, or in combination with one or more other materials.

By way of example, the IC device extension may be formed by curing the silicon such as to a desired crosslink structure to hold a predetermined shape in which the IC device extension is positioned during curing. Once the IC device extension is cured to the desired cross link structure, the IC device extension is retains the predetermined "preload" shape.

Figure 5A:
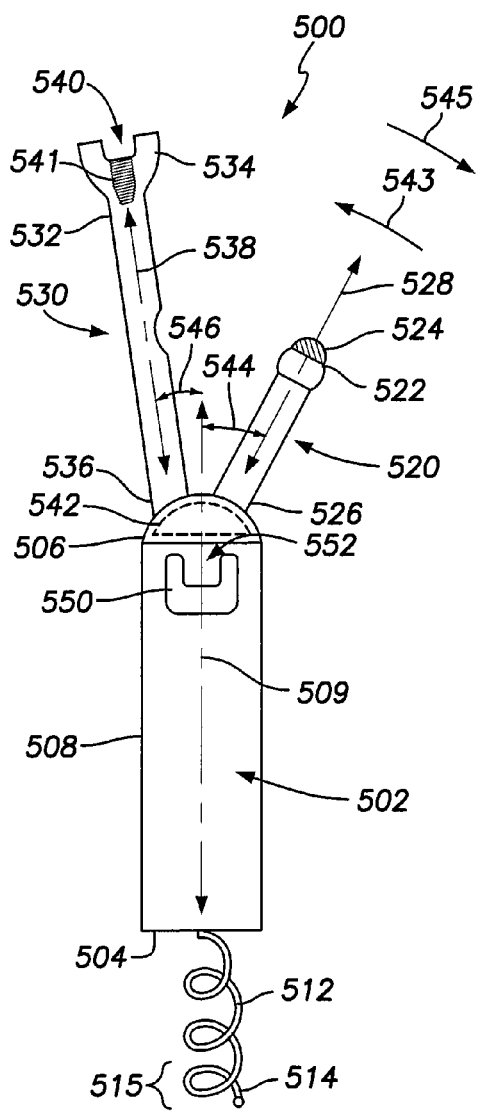
FIG. 5A illustrates a LIMD formed in accordance with an alternative embodiment, including an appendage arm and a stabilizer arm.

FIG. 5A illustrates an LIMD 500 formed in accordance with an alternative embodiment. The LIMD 500 includes a body or housing 502 having a shell 508 that hermetically encloses the electronics, controller, battery, charge storage unit, and all other electrical components of the LIMD 500. The housing 502 has a proximal base 504 and a distal top end 506, with the intermediate shell 508 extending there between. The shell 508 is elongated and may be tubular in shape to extend along a longitudinal axis 509. The base 504 includes at least one electrode 512. The electrode 512 may be a helical shaped screw to actively secure the base 504 at a desired site within a selected local chamber of the heart. The electrode 512 includes a conductor that is surrounded by insulation along the majority of the length thereof, but exposes the distal tip 514 of the conductor, such that the electrode 512 only delivers stimulus pulses and senses electrical activity in the region denoted at 515 which corresponds to an distal activation site proximate an adjacent chamber wall (and distal from the local chamber in which the LIMD 500 is implanted).

The LIMD 500 further includes an appendage arm 520 pivotally connected to and extending outward from the top end 506. The appendage arm 520 includes a distal end 522 upon which an electrode 524 is located. The electrode 524 may be a passive electrode that is configured to simply rest against a select activation site. Alternatively, the electrode 524 may be an active fixation electrode that is configured to be secured to the tissue at the activation site (e.g. through a helix, spike, serrated edge, barb, and the like).

The appendage arm 520 includes a proximal end 526 that is rotatably coupled through a hinge assembly 542 to the top end 506 of the housing 502. The appendage arm 520 extends along an appendage axis 528 and rotates along the appendage rotation arc 544 between limits. The hinge assembly 542 is configured to permit the appendage arm 520 to rotate from a collapsed installation position to a deployed implanted position. When in the collapsed position, the appendage arm 520 is rotated in the direction of arrow 543 until the appendage axis 528 forms a very small acute angle, or is oriented substantially parallel to, a longitudinal axis 509 of the shell 508 of the LIMD 500. When in the deployed position, the appendage arm 520 rotates in the direction of arrow 545 until reaching a fully deployed outer limit of the arc of rotation as defined by the hinge assembly 542. When fully deployed, the appendage axis 528 projects outward at a larger acute angle (e.g. 10-150°) from the longitudinal axis 509 of the shell 508. The outer limit of the deployed position for the appendage arm 520 is controlled by the rotation range permitted at the hinge assembly 542 and may have spring tension tensioning it with respect to the stabilizer arm or the housing 502.

The LIMD 500 also includes a stabilizer arm 530 having a distal end 532 and a proximal end 536. The distal end 532 is formed integral with a pusher cup 534 that includes some type of pusher reception feature, such as a pusher receptacle 540. The pusher cup 534 and receptacle 540 are configured to receive an external pusher tool that is used by the physician when implanting the LIMD 500 (as explained below in more detail). As one example, the pusher receptacle 540 may include a threaded recess 541 that is configured to threadably and securely receive a tip of the pusher tool to ensure a secure attachment to the pusher tool during installation. Once the LIMD 500 is fully implanted, the tip of the pusher tool is unscrewed from the threaded receptacle 541. An expandable collet may be used, instead of a screw to attach the pusher tool to the stabilizer arm 530.

The stabilizer arm 530 is rotatably secured, at its proximal end 536, to the hinge assembly 542 to permit the stabilizer arm 530 to rotate along arc 546. The stabilizer arm 530 may be rotated between a collapsed installation position at which the stabilizer axis 538 is arranged at a very small acute angle or substantially parallel to the longitudinal axis 509. Once implanted, the stabilizer arm 530 is then permitted to rotate outward along arc 546 to a deployed position such that the stabilizer axis 538 forms a larger acute angle (e.g. 10-150°) with respect to the longitudinal axis 509. The hinge assembly 542 controls the range of rotation afforded to the stabilizer arm 530 and may have spring tension tensioning it with respect to the appendage arm 520 or the housing 502. At least one of the stabilizer arm 530 and appendage arm 520 may be constructed to have a core structure that is torque and compression resistant such that when the pusher tool is rotated or moved longitudinally, the stabilizer arm 530 and/or appendage arm 520 conveys rotational and longitudinal force from the pusher tool to the housing of the LIMD 500. For example, the core structure may include a metal (e.g. aluminum or stainless steel) braid encased in a biocompatible material, such as PTFE, ETFE or silicon rubber. The braid may have a hollow core in which insulated conductors run between electrodes and the LIMD 500.

Optionally, the stabilizer arm 530 may be fixedly secured to the distal end 506 of the LIMD 500, such that the stabilizer arm 530 does not rotate relative to the longitudinal axis 509. Instead, in this alternative embodiment, the stabilizer arm 530 is rigidly secured to the distal end 506 and may be oriented such that the stabilizer axis 530 extends directly parallel or at an angle to the longitudinal axis 509 at all times, during installation and after deployment. Again, the stabilizer arm 530 and the appendage arm 520 collectively form an IC device extension.

As a further option, a pusher cup or multiple pusher cups 550 may be provided about the exterior surface of the shell 508 or on the distal top end 506. The pusher cup 550 includes a pusher receptacle 552 configured to receive the tip of a pusher tool that is used during implantation. The pusher cup 550 may be provided in place of, or in addition to, the pusher cup 534. For example, the stabilizer arm 530 may be entirely removed, in which case the pusher cup 550 may be provided on the side or top end 506 of the housing 502. Alternatively, when the stabilizer arm 530 is included, but is too flexible to convey rotational and/or longitudinal force onto the housing 502, then the pusher cup 550 may be included. As a further option, pusher cups 534, 550 may both be included such as when it is desirable to maintain secure connections to the housing 502 and the appendage arm 520 and stabilizer arm 530 while manipulated and navigated to respective implanted positions. For example, once the LIMD 500 is secured to the chamber wall, the introducer may be partially removed, yet one pusher tool or stylet may remain secured to the pusher cup 550 to maintain the LIMD 500 in a desired position and orientation while a second tool manipulates the appendage arm 520 and stabilizer arm 530 to implant positions. In this manner, the tool or stylet in pusher cup 550 prevents excess forces from being applied to the electrode 512 while the arms 520, 530 are navigated to installed positions. Further, the tool or stylet may remain in pusher cup 550 until a separate tool is disconnected from pusher cup 534.

Optionally, a third pusher cup could be located on the distal end of the appendage arm 520 to afford direct control over positioning of the electrode 524.

Figure 5B:
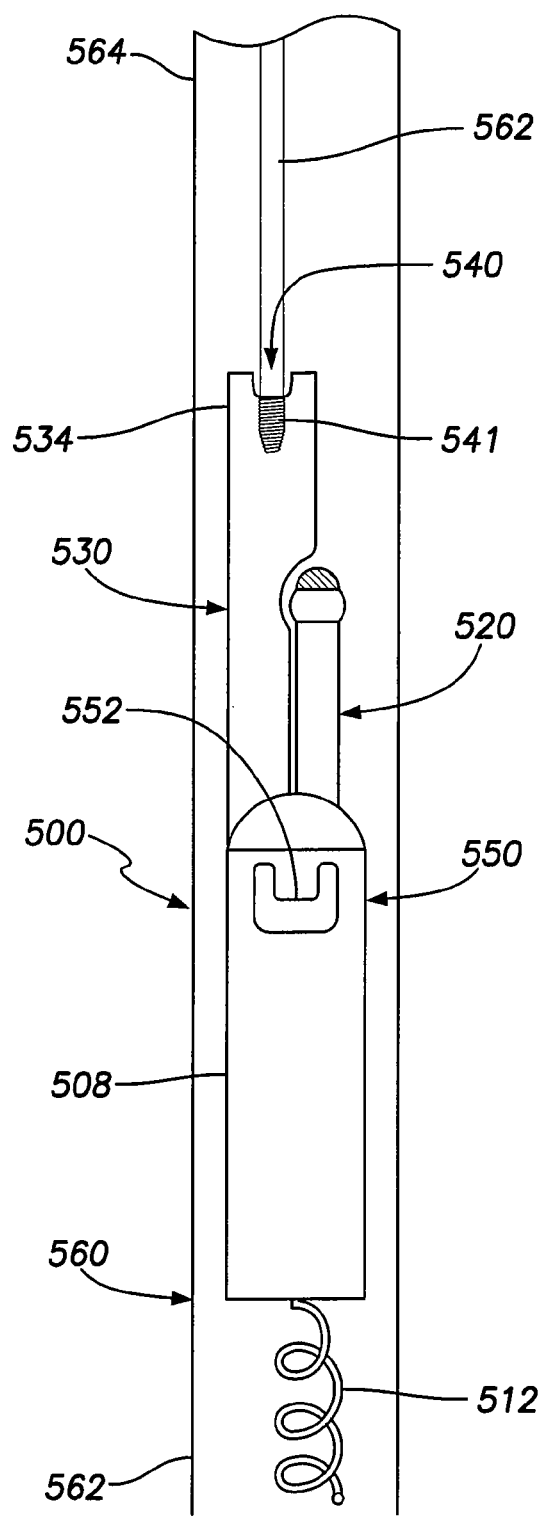
FIG. 5B illustrates the LIMD of FIG. 5A during installation, while rotated within an introducer.

FIG. 5B illustrates the LIMD 500 of FIG. 5A during installation, while located within an introducer 560. The introducer has a distal end 562 that is open to permit the LIMD 500 to be implanted and deployed there through. The introducer 560 includes a proximal end 564 along which a pusher or other form of tool (e.g. a stylet) is used guide the LIMD 500 into position. As shown in FIG. 5B, the stabilizer arm 530 and appendage arm 520 are contracted in their collapsed position to define an outer envelope substantially no greater than the outer envelope of the body 508 of the LIMD 500. The pusher device 562 may engage one or both of the pusher receptacle 540 in the pusher cup 534 and/or the pusher receptacle 552 and the pusher cup 550. During implantation, the pusher or stylet 562 is securely attached at the receptacle cup 534 to guide the LIMD 500 to its activation site. Once the electrode 512 is located against the desired tissue at the activation site, the pusher or stylet 562 may then be rotated to similarly cause the LIMD 500 and electrode 512 to rotate until securely affixed within the select tissue. As one example, the receptacle 540 and/or receptacle 552 may have a noncircular cross section as viewed from the top down (e.g. a rectangular triangle, hexagon, or other polygon shape) such that when the pusher or stylet 562 is rotated, it remains securely fixed within the receptacle 540 to induce rotation at the electrode 512.

Figure 6A:
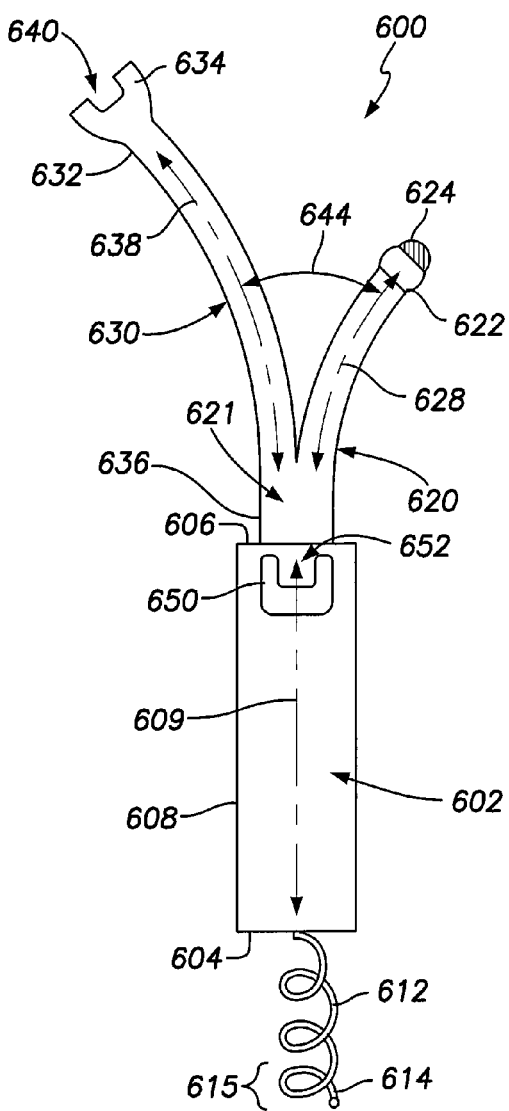
FIG. 6A illustrates a LIMD formed in accordance with an alternative embodiment, in which the appendage arm and stabilizer arm are configured in a manner different than those of FIG. 5A.

FIG. 6A illustrates an LIMD 600 that resembles the LIMD 500, except that the appendage arm 620 and stabilizer arm 630 are configured in a manner different than those of FIG. 5A. In the embodiment of FIG. 6A, the stabilizer arm 630 and appendage arm 620 are integrally joined with one another in a base area 621, but are formed of a flexible material that has a desired preformed resting shape, corresponding to the deployed configuration illustrated in FIG. 6A. When in the deployed position, the stabilizer arms 628, 630 are flared outward away from one another by an angle denoted at 644.

The appendage arm 620 and stabilizer arm 630 have a common proximal end 636 that is secured to the top end 606 of the body 602. The appendage arm 620 has a distal end 622 with an electrode 624 thereon as configured to passively or actively engage tissue at a desired activation site. The stabilizer arm 630 has a distal end 632 at which a pusher cup 634 is formed integral therewith. The pusher cup 634 includes a pusher receptacle 640 that is configured to receive a pusher tool during installation. During installation, the appendage arm 620 and stabilizer arm 630 are flexed inward to collapse against one another such that the angle 644 is very small or approximately zero in order that the appendage axis 628 and stabilizer axis 638 extend substantially parallel to the longitudinal axis 609 of the LIMD 600. When the appendage and stabilizer arms 620, 630 are collapsed against one another, the outer envelope thereof is no greater than the outer envelope of the shell 608 to provide a form factor small enough to be received within an introducer for installation in a desired chamber of the heart.

The LIMD 600 includes a body or housing 602 having a shell 608 that hermetically encloses the electronics, controller, battery, charge storage unit, and all other electrical components of the LIMD 600. The housing 602 has a proximal base 604 and a distal top end 606, with the intermediate shell 608 extending there between. The shell 608 is elongated and may be tubular in shape to extend along a longitudinal axis 609. The base 604 includes at least one electrode 612. The electrode 612 may be a helical shaped screw to actively secure the base 604 at a desired site within a selected local chamber of the heart. The electrode 612 includes a conductor that is surrounded by insulation along the majority of the length thereof, but exposes the distal tip 614 of the conductor, such that the electrode 612 only delivers stimulus pulses and senses electrical activity in the region denoted at 615 which corresponds to an distal activation site proximate to an adjacent chamber wall (and distal from the local chamber in which the LIMD 600 is implanted).

The LIMD 600 further includes an appendage arm 620 pivotally connected to and extending outward from the top end 606. The appendage arm 620 includes a distal end 622 upon which an electrode 624 is located. The electrode 624 may be a passive electrode that is configured to simply rest against a select activation site. Alternatively, the electrode 624 may be an active fixation electrode that is configured to be secured to the tissue at the activation site (e.g. through a helix, spike, serrated edge, barb and the like).

The LIMD 600 also includes a stabilizer arm 630 having a distal end 632 and a proximal end 636. The distal end 632 is formed integral with a pusher cup 634 that includes some type of pusher reception feature, such as a pusher receptacle 640. The pusher cup 634 and receptacle 640 are configured to receive an external pusher tool that is used by the physician when implanting the LIMD 600 (as explained below in more detail). As one example, the pusher receptacle 640 may include a threaded recess 641 that is configured to threadably and securely receive a tip of the pusher tool to ensure a secure attachment to the pusher tool during installation. Once the LIMD 600 is fully implanted, the tip of the pusher tool is unscrewed from the threaded receptacle 641.

The stabilizer arm 630 may be flexed between a collapsed installation position at which the stabilizer axis 638 is arranged at a very small acute angle or substantially parallel to the longitudinal axis 609. Once implanted, the stabilizer arm 630 is then permitted to return to its flared state to a deployed position such that the stabilizer axis 638 forms a larger acute angle (e.g. 10-60°) with respect to the longitudinal axis 609.

Optionally, the stabilizer arm 630 may be fixedly secured to the distal end 606 of the LIMD 600, such that the stabilizer arm 630 does not rotate relative to the longitudinal axis 609. Instead, in this alternative embodiment, the stabilizer arm 630 is rigidly secured to the distal end 606 and may be oriented such that the stabilizer axis 630 extends directly parallel to the longitudinal axis 609 at all times, during installation and after deployment. Again, the stabilizer arm 630 and the appendage arm 620 collectively form an IC device extension.

As a further option, a pusher cup or multiple pusher cups 650 may be provided about the exterior surface of the shell 608. The pusher cup 650 includes a pusher receptacle 652 configured to receive the tip of a pusher tool that is used during implantation. As explained above in connection with FIG. 5A, one or more pusher cups may be provided in various locations.

Figure 6B:
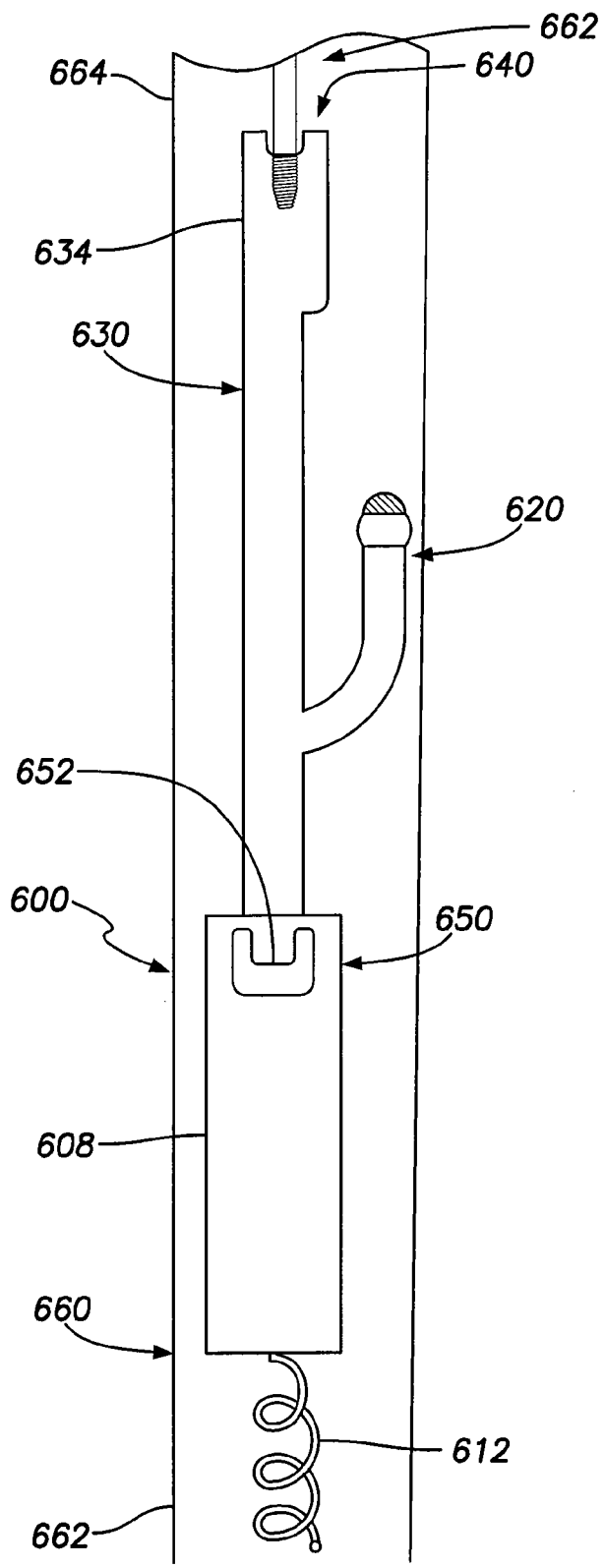
FIG. 6B illustrates the LIMD of FIG. 6A during installation, while located within an introducer.

FIG. 6B illustrates the LIMD 600 of FIG. 6A during installation, while located within an introducer 660. The introducer has a distal end 662 that is open to permit the LIMD 600 to be implanted and deployed there through. The introducer 660 includes a proximal end 664 along which a pusher or other form of tool (e.g. a stylet) is used guide the LIMD 600 into position. As shown in FIG. 6B, the stabilizer arm 630 and appendage arm 620 are contracted in their collapsed position to define an outer envelope substantially no greater than the outer envelope of the body 608 of the LIMD 600. The pusher device 662 may engage one or both of the pusher receptacle 640 in the pusher cup 634 and/or the pusher receptacle 652 and the pusher cup 650. During implantation, the pusher or stylet 662 is securely attached at the receptacle cup 634 to guide the LIMD 600 to its activation site. Once the electrode 612 is located against the desired tissue at the activation site, the pusher or stylet 662 may then be rotated to similarly cause the LIMD 600 and electrode 612 to rotate until securely affixed within the select tissue. As one example, the receptacle 640 and/or receptacle 652 may have a noncircular cross section as viewed from the top down (e.g. a rectangular triangle, hexagon, or other polygon shape) such that when the pusher or stylet 662 is rotated, it remains securely fixed within the receptacle 640 to induce rotation at the electrode 612.

Figure 7A:
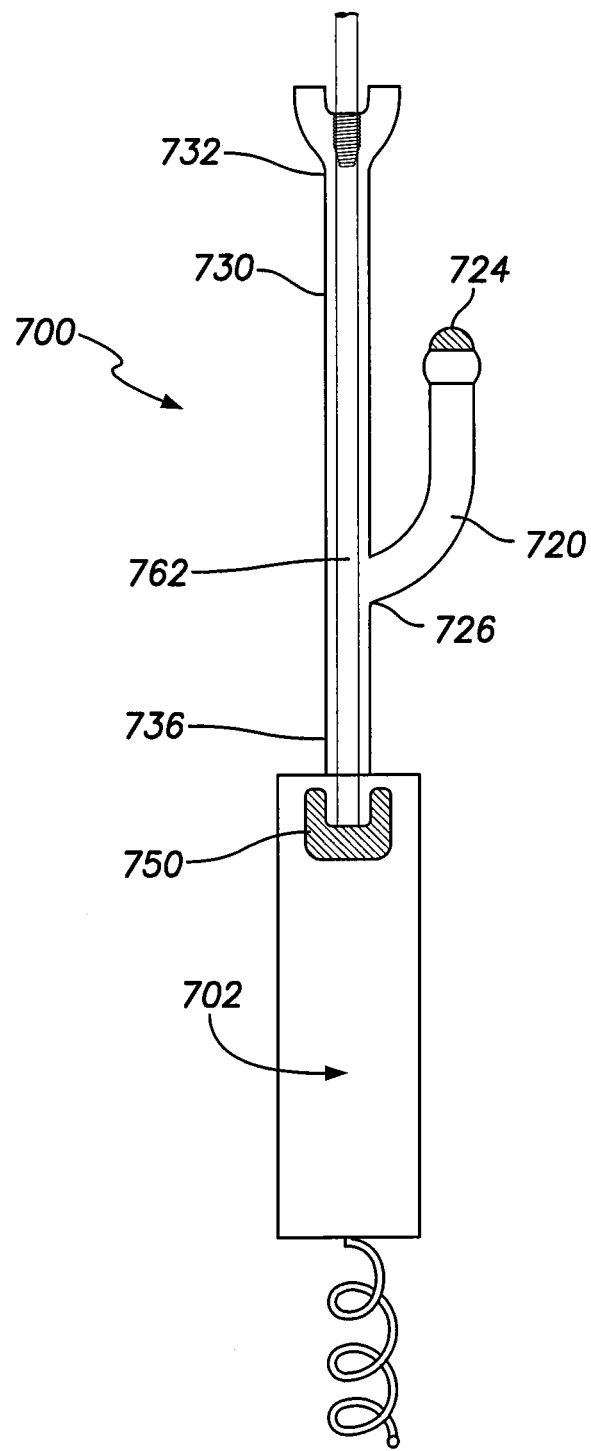
FIG. 7A illustrates an alternative embodiment for a LIMD in a collapsed installation configuration.
Figure 7B:
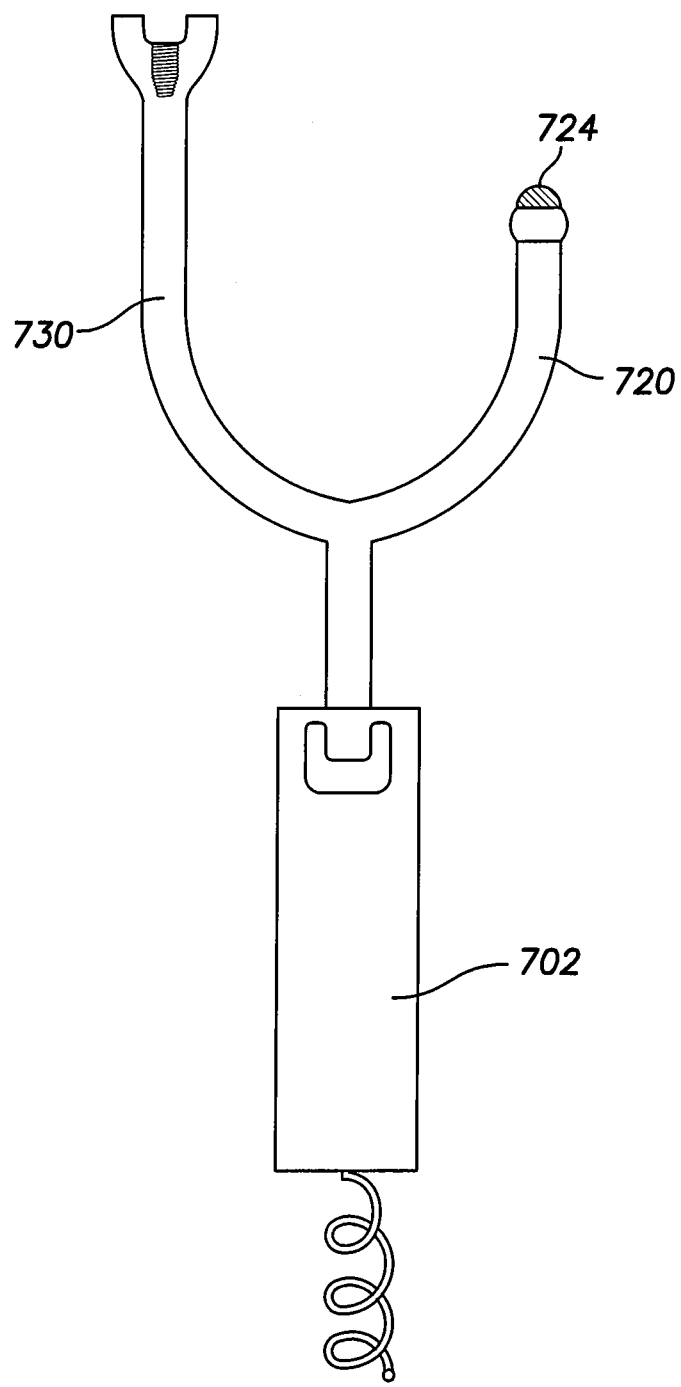
FIG. 7B illustrates the LIMD of FIG. 7A in a deployed flared position.

FIGS. 7A and 7B illustrate an alternative embodiment for an LIMD 700 when in the collapsed installation configuration (FIG. 7A) and in the deployed flared position (FIG. 7B). The LIMD 700 includes a stabilizer arm 730 having a distal and proximal end 732, 736. An appendage arm 720 is integrally formed, with and extends outward at an intermediate position from, the stabilizer arm 730. The appendage arm 720 includes a proximal end 726 that is joined to the stabilizer arm 730 at an intermediate position away from the body 702 of the LIMD 700. The appendage arm 720 includes an electrode 724 on the distal end thereof. As shown in FIG. 7A, before deployment and while in the collapsed position, the appendage arm 720 does still slightly project outward beyond the outer envelope of the body 702, but the stabilizer arm 730 extends along the direction substantially parallel to the longitudinal axis of the body 702. In the example of FIG. 7A, the pusher cup 750 is located at the distal top end of the body 702. The stabilizer arm 730 has a hollow passage there through that receives a tool 762 that pushes the LIMD 700 to a desired deployed position. For example, the passage through the stabilizer arm 730 aligns with the pusher cup 750 in the distal top end such that the tool 762 is inserted into the passage until securely engaging the pusher cup 750. When in the passage, the tool 762 maintains the stabilizer arm 730 in a straight, elongated shape extending along the longitudinal axis of the tool 762.

Turning to FIG. 7B, once the LIMD 700 is implanted and the introducer and tool 762 removed, the stabilizer arm 730 and appendage arm 720 are permitted to flare outward to form a Y-shaped configuration. It should be recognized that the shape formed by the stabilizer arm 730 and appendage arm 720 after deployment may be modified and controlled during construction to achieve a desired final configuration when implanted. By removing the tool 762, the stabilizer arm 730 is permitted to return to its natural pre-formed shape.

Figure 5C:
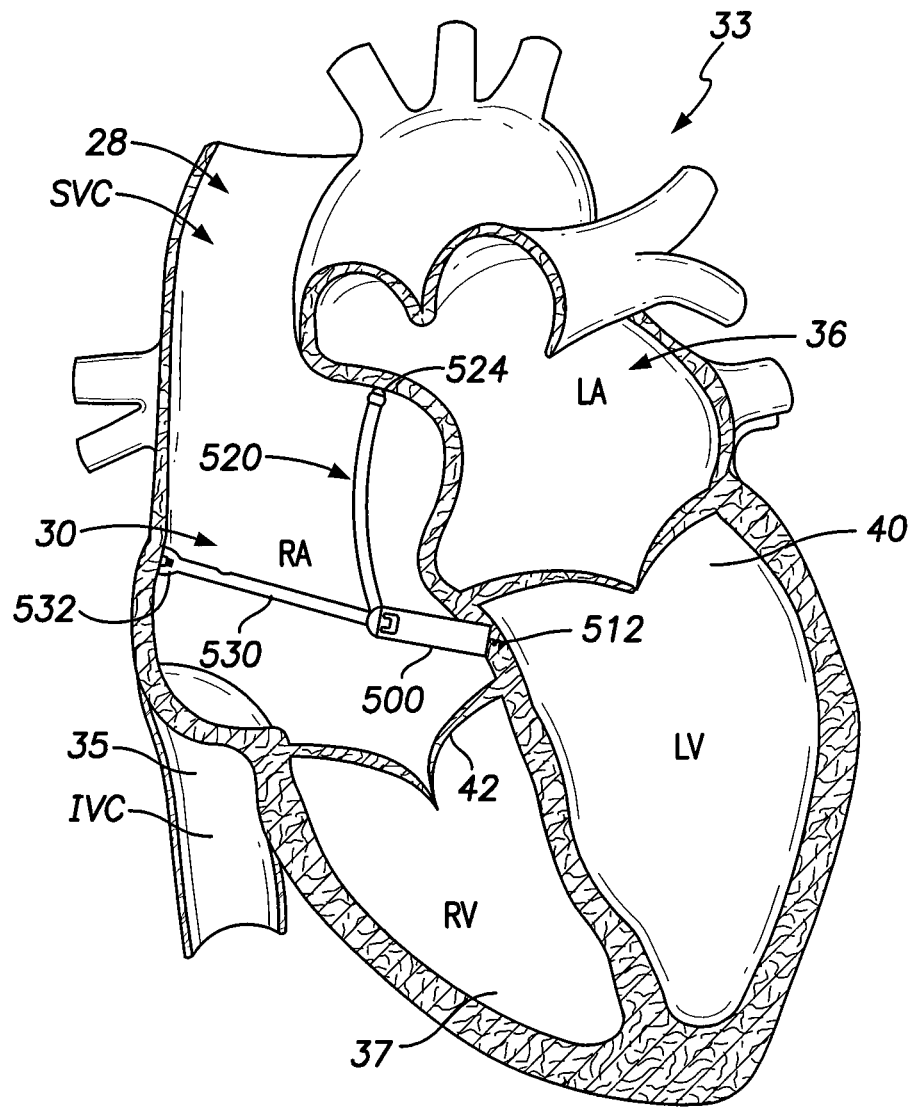
FIG. 5C illustrates the LIMD of FIG. 5A in an exemplary deployed position within a heart.

FIG. 5C illustrates the LIMD 500 in an exemplary deployed position. When deployed as illustrated in FIG. 5C, the LIMD 500 may be located directly against the ventricular vestibule. The electrode 512 is secured to the ventricular vestibule and/or extended to a point such that the distal end of the electrode 512 projects into or is located directly against the surface tissue of the right ventricle. The appendage arm 520 is flared to its deployed position to locate the electrode 524 against atrial tissue in the atrial appendage area. In the example of FIGS. 5A-5C, the electrode 524 is configured to simply be pressed against the tissue at the atrial appendage. Optionally, spikes or a serrated edge or other fixation means may be added to the electrode at 524 to further facilitate engagement to the tissue in the atrial appendage.

When deployed and in the flared position, the stabilizer arm 530 extends into the SVC and rests against the side of the SVC to provide stabilization for the overall positioning of the LIMD 500. It should be recognized, that throughout operation, as the right atrium moves during contraction, the stabilizer arm 530 and appendage arm 520 constantly pivot, rotate and/or flex to avoid interference with the normal mechanical movement of the right atrium.

Figure 6C:
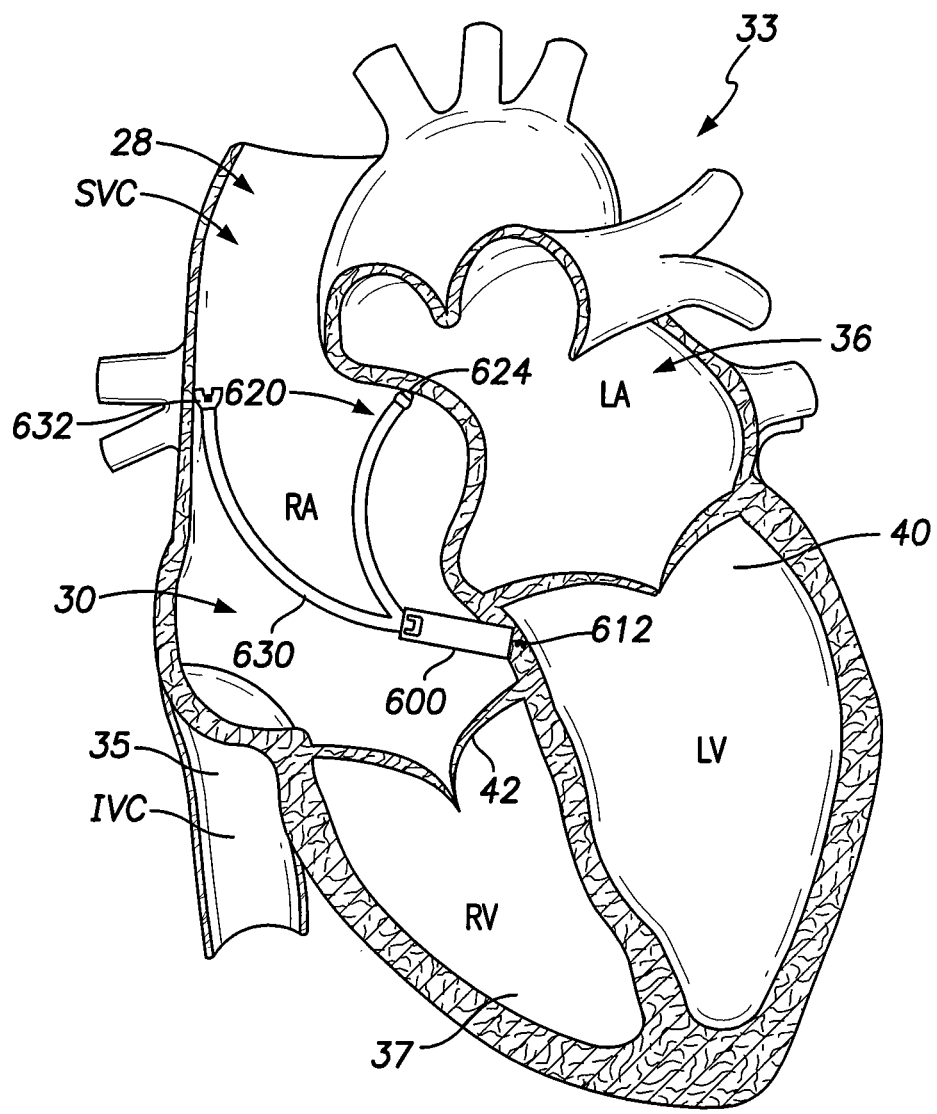
FIG. 6C illustrates the LIMD of FIG. 6A in an exemplary deployed position within a heart.

FIG. 6C illustrates an exemplary deployment of the LIMD 600 when located in the right atrium. The electrode 612 is securely affixed through the ventricular vestibule and/or locate the distal end thereof within or immediately adjacent the surface of the right ventricular wall. The appendage arm 620 is flared to a deployed position to locate the electrode 624 in the atrial appendage. The stabilizer arm 630 is also flared in the opposite direction to its deployed position such that the distal end 632 extends into and engages tissue within the SVC. As explained above, the appendage arm 620 and stabilizer arm 630 are flexible and will constantly move in connection with the mechanical contraction of the right atrium to avoid interference with the normal mechanical movement of the heart.

As shown in FIGS. 5A-5C, 6A-6C, and 7A-7B, the LIMD may be provided with two or more fixation mechanisms at the top end of the device body. One fixation mechanism, which is not electrically active, acts as to stabilize and passively-fixate the LIMD 300 in the superior vena cava (SVC). The other fixation mechanism is shorter but has an electrode at its tip and has the dual role of passive fixation to the RA appendage and pacing and sensing the RA. Additionally, the LIMD 300 has two or more possible configurations for attachment to the implant (and possibly explant) tool at either the end of the SVC stabilization fixation mechanism or at the side of the LIMD body. When the LIMD is affixed to the desired target site and the introducer (which protects blood vessels and myocardium from being damaged by the helical cathode) is removed, the passive fixation mechanisms swivel away from the longitudinal axis of the LIMD and contact their respective sites. The degree by which these fixation mechanisms swivel away from each other may be pre-determined or controlled by a ratcheting mechanism via the implant tool. Alternatively, the LIMD may use a stylet after affixation to the target site, which transmutes the morphology of the fixation mechanisms from a "J-shape" to a "U-shape," as shown in FIG. 7B.

In FIGS. 5C and 6C, the LLPM is affixed to the target site on the atrioventricular wall and is deployed in the RA. Here, it can be seen that there are three points of contact between the LIMD and myocardium, significantly reducing the possibility of dislodgement. In addition, dual chamber (e.g. DDD or DDDR mode) functionality is achieved via the RA appendage fixation mechanism (which paces and senses the RA) and the helical cathode electrode (which paces and senses the RV).

If dual-chamber pacing and sensing is achieved with a long helical fixation electrode covered proximally with insulation, it may be desirable to know when the helix has extended through the myocardium to the adjacent chamber. This may be determined using real-time impedance measurement between the helical tip electrode and another electrode. When the helical electrode is in pooled blood of any heart chamber, characteristic low impedance will be between it and any other electrode in the blood. As the helical electrode is screwed into the myocardium, impedance will rise. When the helix has been affixed sufficiently to break through the wall to the other chamber, impedance will drop. The changes in impedance may be used to know how far to screw in the helix, which portions of walls delineating heart chambers are an appropriate thickness for the helix, and whether any other spacer is needed to prevent the device from torqueing with the heart's mechanical motion.

Before disconnecting from the insertion tool, a pacing test provides an indication of the chamber paced and capture threshold. If the test shows that pacing is not occurring in the desired chamber or that thresholds are inappropriate, the tool may be used to remove the fixation and attempt to attach at another location.

For each attempt, the distance traversed by the lead's AV helix through the wall between the RA and RV between each turn of the screw may be closely controlled. Atrial and ventricular capture thresholds may be recorded with a pacing system analyzer (PSA) between each turn or at set degrees of rotation. The PSA may use the electrodes on the LIMD or may use electrodes on the exterior or outer end of the introducer to test for capture thresholds prior to affixing the LIMD in place. The distance between each turn may be generally between 0.5 to 2.0 mm. For example, all lead helical electrodes may be coated with an insulating material such as Parylene®-coated except for the most distal portion of the pitch of the screws (thus ensuring that only tissue near the tip is stimulated). For example, the helical electrode may be advanced in small increments, and after each increment, the PSA may then test for a capture. An interactive process may be repeated whereby the electrode is advanced and then the PSA determines if a capture threshold has been satisfied. This process is repeated until impulses from the distal electrode capture the ventricular tissue. Similarly, a capture test may be performed for the atrial electrode. The atrial electrode is adjusted until the PSA confirms atrial capture. In accordance with the foregoing, it is possible for an AV helical electrode on a lead to burrow from the RA and excite ventricular tissue. This allows a dual chamber mode-capable LIMD to have its main body located in the one chamber and pace and sense another chamber.

The term "distal" as used to describe wall tissue and activation sites, is used with respect to the local chamber.

Figure 8:
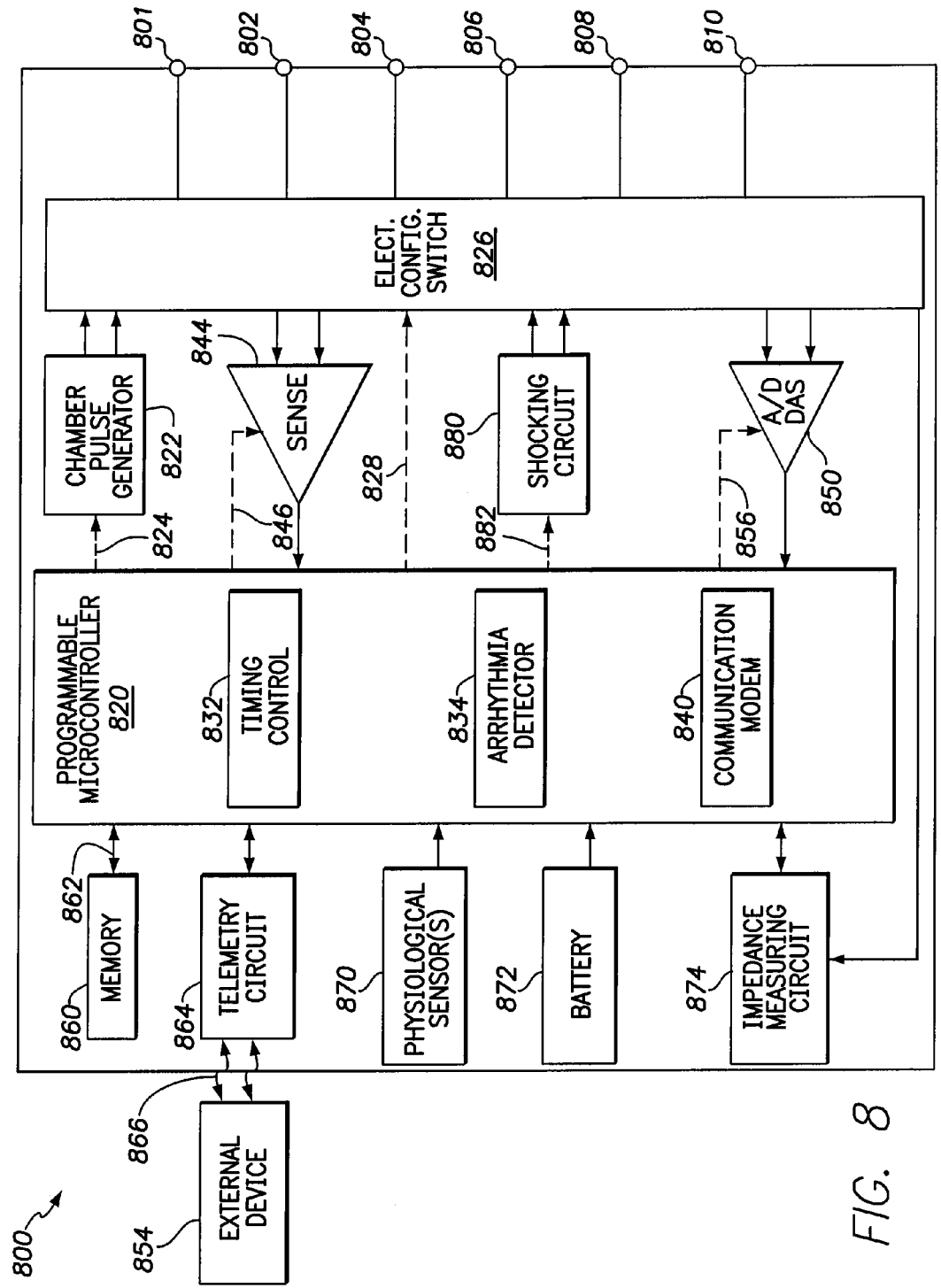
FIG. 8 illustrates an exemplary block diagram of the electrical components of an LIMD.

FIG. 8 shows an exemplary LIMD 800 configured for dual-chamber functionality from a primary location within a single chamber of the heart. For example, the LIMD 800 may be implemented as a pacemaker, equipped with both atrial and ventricular sensing and pacing circuitry. Alternatively, the LIMD 800 may be implemented with a reduced set of functions and components. For instance, the LIMD 800 may be implemented without ventricular sensing and pacing. The LIMD 800 may also be implemented with an increased set of functions. For example, if the LIMD 800 includes a coil type electrode, the LIMD may be configured to include cardioversion and/or shocking therapy capability.

The LIMD 800 has a housing 801 to hold the electronic/computing components. The housing 801 (which is often referred to as the "can", "case", "encasing", or "case electrode") may be programmably selected to act as the return electrode for certain stimulus modes. Housing 801 further includes a plurality of terminals 802, 804, 806, 808, 810 that interface with electrodes of the LIMD. For example, the terminals may include: a terminal 802 that connects with a first electrode associated with the housing (e.g. electrode 410) and located in a first chamber; a terminal 804 that connects with a second electrode associated with the housing (e.g., electrode 411) and also located in the first chamber; a terminal 806 that connects with a third electrode associated with the housing (e.g. electrode 412) and located in the first chamber and possibly partially extending into tissue associated with a second chamber; and two additional terminals 808, 810 that connect with one or more additional electrodes (e.g., electrode 524), if available. The type and location of each electrode may vary. For example, the electrodes may include various combinations of ring, tip, coil and shocking electrodes and the like.

The LIMD 800 includes a programmable microcontroller 820 that controls various operations of the LIMD 800, including cardiac monitoring and stimulation therapy. Microcontroller 820 includes a microprocessor (or equivalent control circuitry), RAM and/or ROM memory, logic and timing circuitry, state machine circuitry, and I/O circuitry.

LIMD 800 further includes a first chamber pulse generator 822 that generates stimulation pulses for delivery by one or more electrodes coupled thereto. The pulse generator 822 is controlled by the microcontroller 820 via control signal 824. The pulse generator 822 is coupled to the select electrode(s) via an electrode configuration switch 826, which includes multiple switches for connecting the desired electrodes to the appropriate I/O circuits, thereby facilitating electrode programmability. The switch 826 is controlled by a control signal 828 from the microcontroller 820.

In the example of FIG. 8, a single pulse generator 822 is illustrated. Optionally, the LIMD 800 may include multiple pulse generators, similar to pulse generator 822, where each pulse generator is coupled to one or more electrodes and controlled by the microcontroller 820 to deliver select stimulus pulse(s) to the corresponding one or more electrodes.

Microcontroller 820 is illustrated as including timing control circuitry 832 to control the timing of the stimulation pulses (e.g., pacing rate, atrio-ventricular (AV) delay etc.). The timing control circuitry 832 may also be used for the timing of refractory periods, blanking intervals, noise detection windows, evoked response windows, alert intervals, marker channel timing, and so on. Microcontroller 820 also has an arrhythmia detector 834 for detecting arrhythmia conditions. Although not shown, the microcontroller 820 may further include other dedicated circuitry and/or firmware/software components that assist in monitoring various conditions of the patient's heart and managing pacing therapies.

The LIMD 800 includes sensing circuitry 844 selectively coupled to one or more electrodes through the switch 826. The sensing circuitry detects the presence of cardiac activity in the right chambers of the heart. The sensing circuitry 844 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit 802 to sense low amplitude signal characteristics of atrial fibrillation. Switch 826 determines the sensing polarity of the cardiac signal by selectively closing the appropriate switches. In this way, the clinician may program the sensing polarity independent of the stimulation polarity.

The output of the sensing circuitry 844 is connected to the microcontroller 820 which, in turn, triggers or inhibits the pulse generator 822 in response to the absence or presence of cardiac activity. The sensing circuitry 844 receives a control signal 846 from the microcontroller 820 for purposes of controlling the gain, threshold, polarization charge removal circuitry (not shown), and the timing of any blocking circuitry (not shown) coupled to the inputs of the sensing circuitry.

In the example of FIG. 8, a single sensing circuit 844 is illustrated. Optionally, the LIMD 800 may include multiple sensing circuit, similar to sensing circuit 844, where each sensing circuit is coupled to one or more electrodes and controlled by the microcontroller 820 to sense electrical activity detected at the corresponding one or more electrodes. The sensing circuit 844 may operate in a unipolar sensing configuration or in a bipolar sensing configuration.

The LIMD 800 further includes an analog-to-digital (ND) data acquisition system (DAS) 850 coupled to one or more electrodes via the switch 826 to sample cardiac signals across any pair of desired electrodes. The data acquisition system 850 is configured to acquire intracardiac electrogram signals, convert the raw analog data into digital data, and store the digital data for later processing and/or telemetric transmission to an external device 854 (e.g., a programmer, local transceiver, or a diagnostic system analyzer). The data acquisition system 850 is controlled by a control signal 856 from the microcontroller 820.

The microcontroller 820 is coupled to a memory 860 by a suitable data/address bus 862. The programmable operating parameters used by the microcontroller 820 are stored in memory 860 and used to customize the operation of the LIMD 800 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 808 within each respective tier of therapy.

The operating parameters of the LIMD 800 may be non-invasively programmed into the memory 860 through a telemetry circuit 864 in telemetric communication via communication link 866 with the external device 854. The telemetry circuit 864 allows intracardiac electrograms and status information relating to the operation of the LIMD 800 (as contained in the microcontroller 820 or memory 860) to be sent to the external device 854 through the established communication link 866.

The IMD 802 can further include magnet detection circuitry (not shown), coupled to the microcontroller 820, to detect when a magnet is placed over the unit. A magnet may be used by a clinician to perform various test functions of the unit 802 and/or to signal the microcontroller 820 that the external programmer 854 is in place to receive or transmit data to the microcontroller 820 through the telemetry circuits 864.

The LIMD 800 may be equipped with a communication modem (modulator/demodulator) 840 to enable wireless communication with a remote device, such as a second implanted LIMD in a master/slave arrangement, such as described in U.S. Pat. No. 7,630,767. In one implementation, the communication modem 840 uses high frequency modulation. As one example, the modem 840 transmits signals between a pair of LIMD electrodes, such as between the can 800 and anyone of the electrodes connected to terminals 802-810. The signals are transmitted in a high frequency range of approximately 20-80 kHz, as such signals travel through the body tissue in fluids without stimulating the heart or being felt by the patient. The communication modem 840 may be implemented in hardware as part of the microcontroller 820, or as software/firmware instructions programmed into and executed by the microcontroller 820. Alternatively, the modem 840 may reside separately from the microcontroller as a standalone component.

The LIMD 800 can further include one or more physiologic sensors 870. Such sensors are commonly referred to as "rate-responsive" sensors because they are typically used to adjust pacing stimulation rates according to the exercise state of the patient. However, the physiological sensor 870 may further be used to detect changes in cardiac output, changes in the physiological condition of the heart, or diurnal changes in activity (e.g., detecting sleep and wake states). Signals generated by the physiological sensors 870 are passed to the microcontroller 820 for analysis. The microcontroller 820 responds by adjusting the various pacing parameters (such as rate, AV Delay, V-V Delay, etc.) at which the atrial and ventricular pacing pulses are administered. While shown as being included within the unit 802, the physiologic sensor(s) 870 may be external to the unit 802, yet still be implanted within or carried by the patient. Examples of physiologic sensors might include sensors that, for example, sense respiration rate, pH of blood, ventricular gradient, activity, position/posture, temperature, minute ventilation (MV), and so forth.

A battery 872 provides operating power to all of the components in the LIMD 800. The battery 872 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 872 also desirably has a predictable discharge characteristic so that elective replacement time can be detected. As one example, the unit 802 employs lithium/silver vanadium oxide batteries.

The LIMD 800 further includes an impedance measuring circuit 874, which can be used for many things, including: impedance surveillance during the acute and chronic phases for proper LIMD positioning or dislodgement; detecting operable electrodes and automatically switching to an operable pair if dislodgement occurs; measuring respiration or minute ventilation; measuring thoracic impedance; detecting when the device has been implanted; measuring stroke volume; and detecting the opening of heart valves; and so forth.

The impedance measuring circuit 874 is coupled to the switch 826 so that any desired electrode may be used.

The microcontroller 820 further controls a shocking circuit 880 by way of a control signal 882. The shocking circuit 880 generates shocking pulses of low (e.g., up to 0.5 joules), moderate (e.g., 0.5-10 joules), or high energy (e.g., 811 to 40 joules), as controlled by the microcontroller 820. Such shocking pulses are applied to the patient's heart 808 through shocking electrodes, if available on the LIMD. It is noted that the shock therapy circuitry is optional and may not be implemented in the LIMD, as the various LIMDs described above and further below will typically not be configured to deliver high voltage shock pulses. On the other hand, it should be recognized that an LIMD may be used within a system that includes backup shock capabilities, and hence such shock therapy circuitry may be included in the LIMD.

Figure 9A:
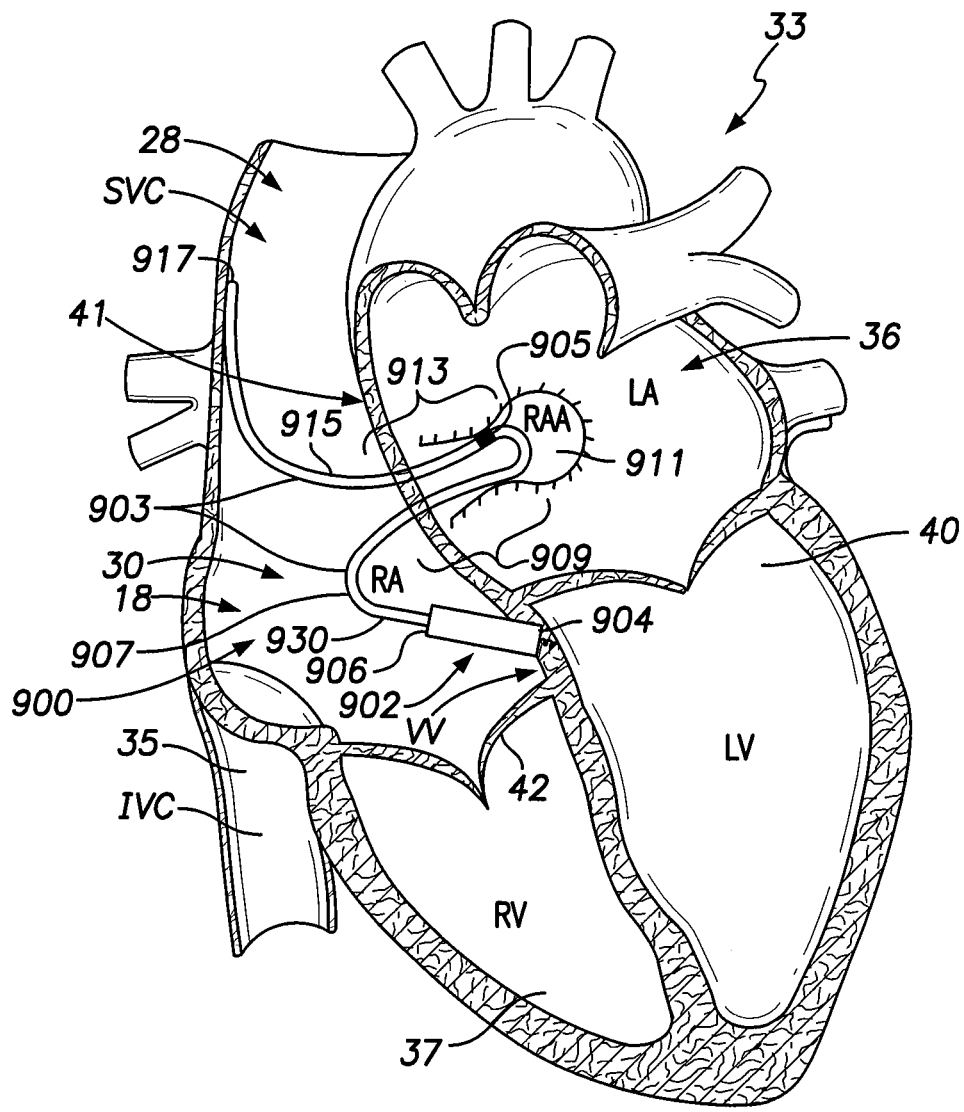
FIG. 9A illustrates a sectional view of a patient's heart and a LIMD having a shaped intra-cardiac (IC) device extension.

FIG. 9A provides a sectional view of a patient's heart 33 and shows an LIMD 900. The LIMD 900 may have been placed through the superior vena cava 28 into the right atrium 30 of the heart 33. The LIMD 900 comprises a housing 902 configured to be implanted entirely within a single local chamber of the heart. The housing 902 includes a proximal base end 904 and a distal top end 906. The proximal base end 904 includes an active fixation member, such as a helix, that is illustrated to be implanted in the ventricular vestibule (VV). A shaped intra-cardiac (IC) device extension 903 extends from the distal top end 906 of the housing 902. The IC device extension 903 comprises an elongated body that may be tubular in shape and may include a metal braid provided along at least a portion of the length therein (as explained herein in more detail). The extension body including a transition sub-segment, an active interim-segment and a stabilizer end-segment, all of which are illustrated in a deployed configuration and some of which are preloaded against anatomical portions of tissue of interest. For example, the active interim-segment (e.g., second curved segment 911, and all or portions of the first and second linear regions 909 and 913) and the stabilizer end-segment (e.g., third curved segment 915 and all or portions of the second linear region 913) are shown preloaded against anatomical tissue of interest. The braid resists torque compression but permits lateral flex. One or more electrodes 905 are carried by the IC device extension 903 and are electrically connected to electronics within the housing 902 through conductors extending through the body of the IC device extension.

The IC device extension 903 is formed with shape memory characteristics that allow the IC device extension 903 to transform between a collapsed state, in which the IC device extension assumes a substantially linear shape, and an expanded state, in which the IC device extension assumes a multiple curved shape, such as shown in FIGS. 9A-9D. In one embodiment, the curved configuration of the IC device extension 903 comprises multiple sharply curved segments, obtusely curved segments, generally linear regions and the like. The number, length, and order of the segments and regions, as well as the degree to which individual segments or regions are curved or linear may vary depending upon the anatomical contour to be followed.

The IC device extension includes a short stem 930 that extends a short distance from the distal top end 906 of the housing 902. The stem 930 merges into a first curved segment 907 that turns at a sharp angle with respect to a longitudinal axis of the housing 902. Optionally, the first curved segment 907 may form an acute angle, 90 degree angle, or obtuse angle approximately with respect to a longitudinal axis of the housing 902. The first curved segment 907 merges into and is followed by a first generally linear region 909 that extends laterally from the housing 902, along a lateral axis, until merging with a second curved segment 911. The second curved segment 911 turns at a sharp angle with respect to the longitudinal axis of the housing 902 and the lateral axis of the first linear region 909. Optionally, the second curved segment 911 may form an acute angle, 90 degree angle, or obtuse angle approximately with respect to the lateral axis of the first linear region 909. As one example, the second curved segment 911 may approximate a 180 degree sharp or "hairpin" curve away from the lateral axis of the first linear region 909 and away from the longitudinal axis of the housing 902. The second curved segment 911 merges into and is followed by a second generally linear region 913 that extends along a second lateral direction.

One or more electrodes 905 are located along the second curved segment 911. Optionally, the electrode(s) may be provided in the region proximate to the junction of the second curved segment 911 and the second linear region 913. Optionally, one or more electrodes 905 may be provided along the second linear region 913.

The second linear region 913 merges with and extends to a third curved segment 915. The third curved segment 915 follows an extending "slow" arc and then terminates at a tail end 917 of the IC device extension 903. The third curved segment 915 follows a slow arc with respect to the longitudinal axis of the housing 902 and the lateral axis of the first linear region 909. As one example, the third curved segment 915 may approximate a 90 degree turn away from the longitudinal axis of the housing 902 until terminating at the tail end 917 of the IC device extension 902.

The shaped IC device extension 903 is formed into a pre-loaded shape in which the first, second and third curved segments 907, 911 and 915 extend along desired arcuate paths and project from longitudinal/lateral axes at desired pitch, roll and yaw angles, where the pitch, roll and yaw angles are measured from reference angular positions. To avoid overly complicating FIG. 9A, examples of longitudinal/lateral axis, arcuate paths, pitch, roll and yaw angles are shown in the embodiment of FIG. 9E, but are equally applicable to any other embodiments described herein.

With continued reference to FIG. 9A, the LIMD 900 is configured to place the housing 902 in the lower region of the right atrium between the OS and IVC with a distal helix electrode, on the housing 902, in the ventricular vestibule to provide ventricular pacing and sensing. The IC device extension 903 extends upward in the right atrium toward and into the SVC. The IC device extension 903 is configured (length wise and shape wise) such that the second curved segment 911 may be implanted within the right atrial IC device extension (RAA), along with those portions of the first and second linear regions 909, 913 near the second curved segment 911. The configuration in FIG. 9A places the electrode 905 in the RAA to allow for right atrial pacing and sensing. The configuration in FIG. 9A also places the proximal portion of the third curved segment 915 against a wall of the SVC to provide overall stability to the LIMD 900.

Figure 9B:
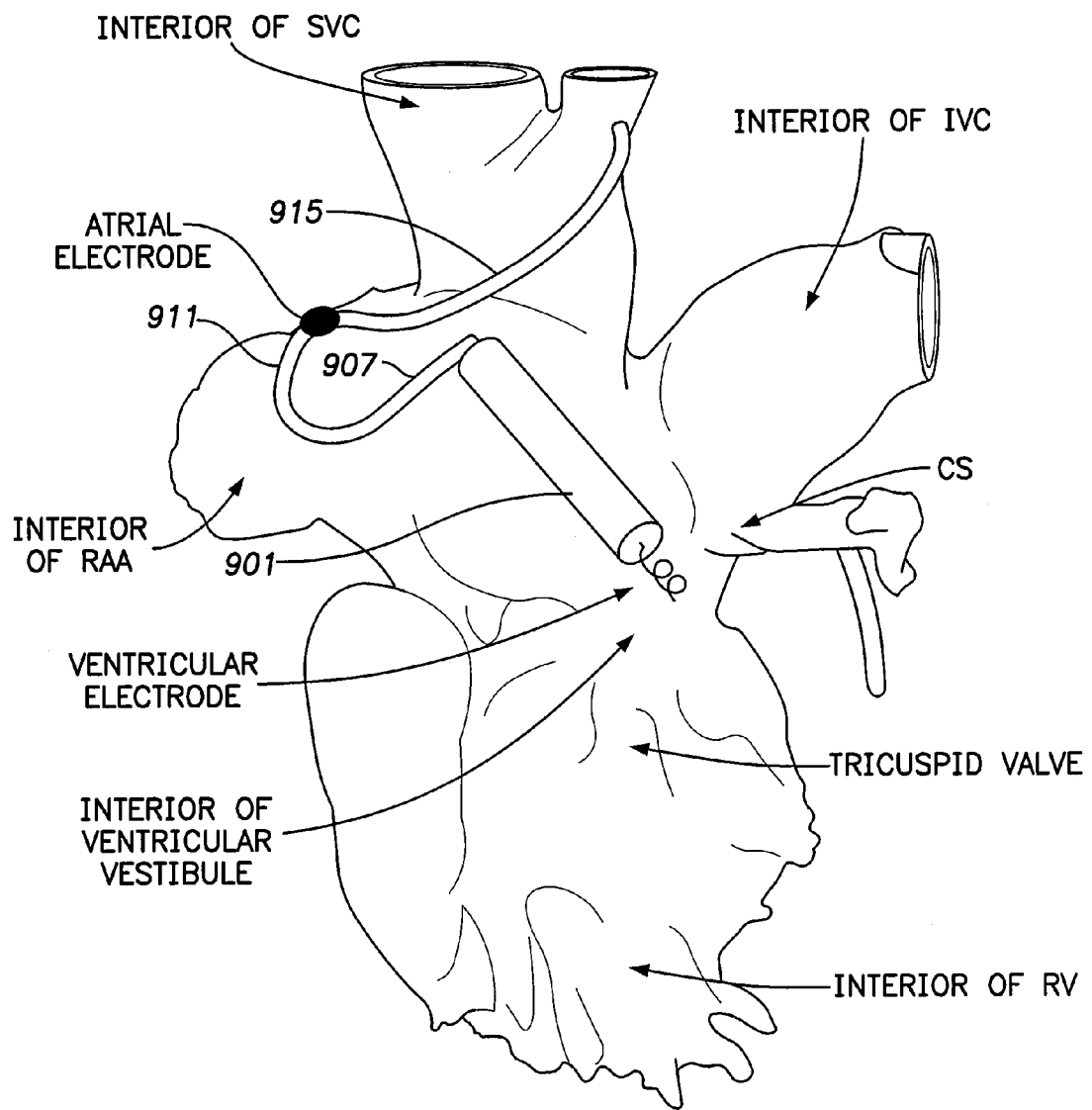
FIG. 9B illustrates a model of an interior of a canine heart and a LIMD having a shaped IC device extension.

FIG. 9B illustrates a model of an interior of a canine heart and shows a leadless implantable medical device having a shaped IC device extension similar to that describe with reference to FIG. 9A. The embodiments of FIGS. 9A and 9B may have IC device extensions that traverse a two-dimensional space, i.e., lie substantially flat in a plane, while extending in x and y directions along its length, or a three-dimensional space, i.e., extending in x, y and z directions along its length.

Figure 9C:
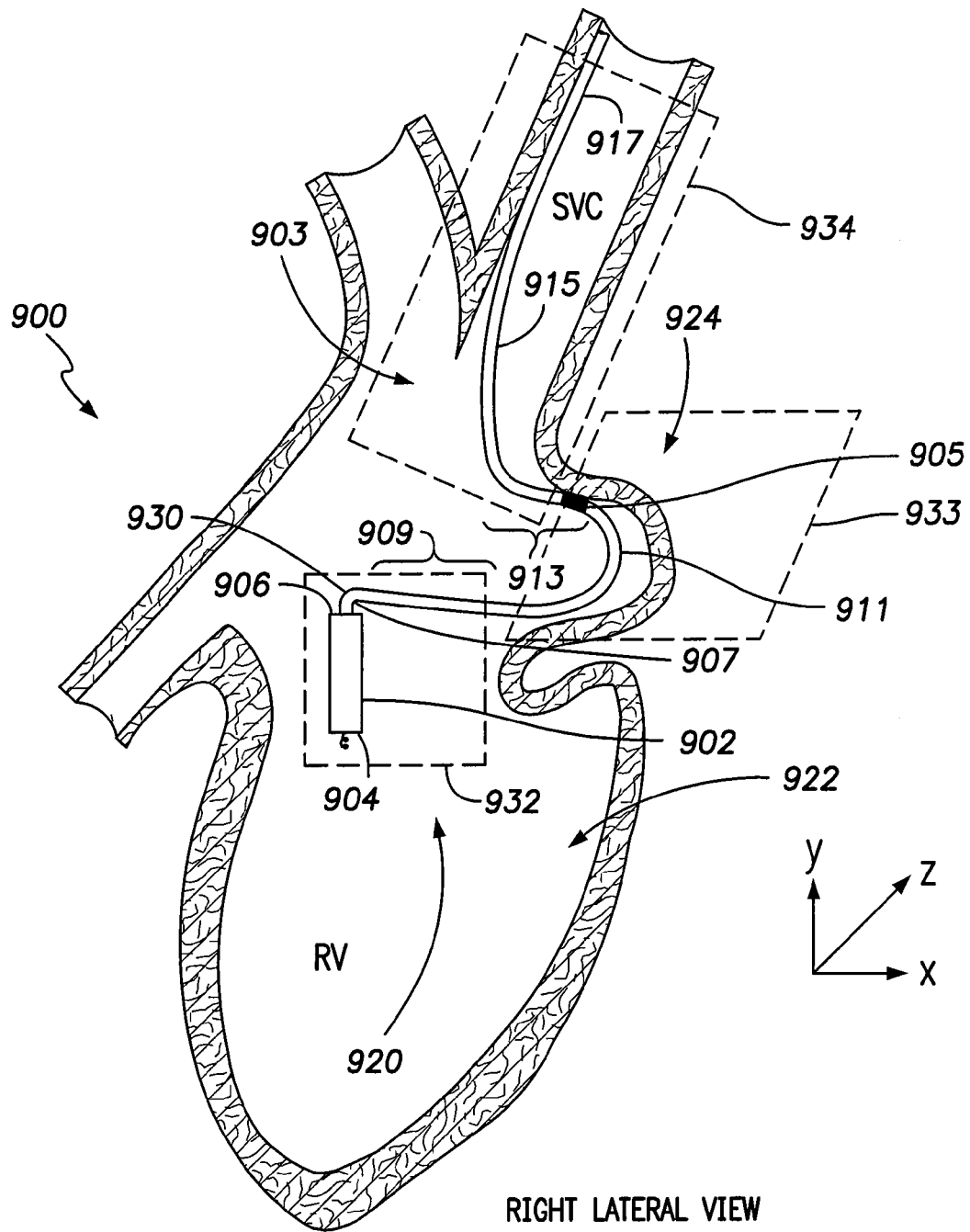
FIG. 9C further illustrates a model of an interior of a human heart and shows an example of the LIMD having the shaped IC device extension described with reference to FIG. 9A.
Figure 9D:
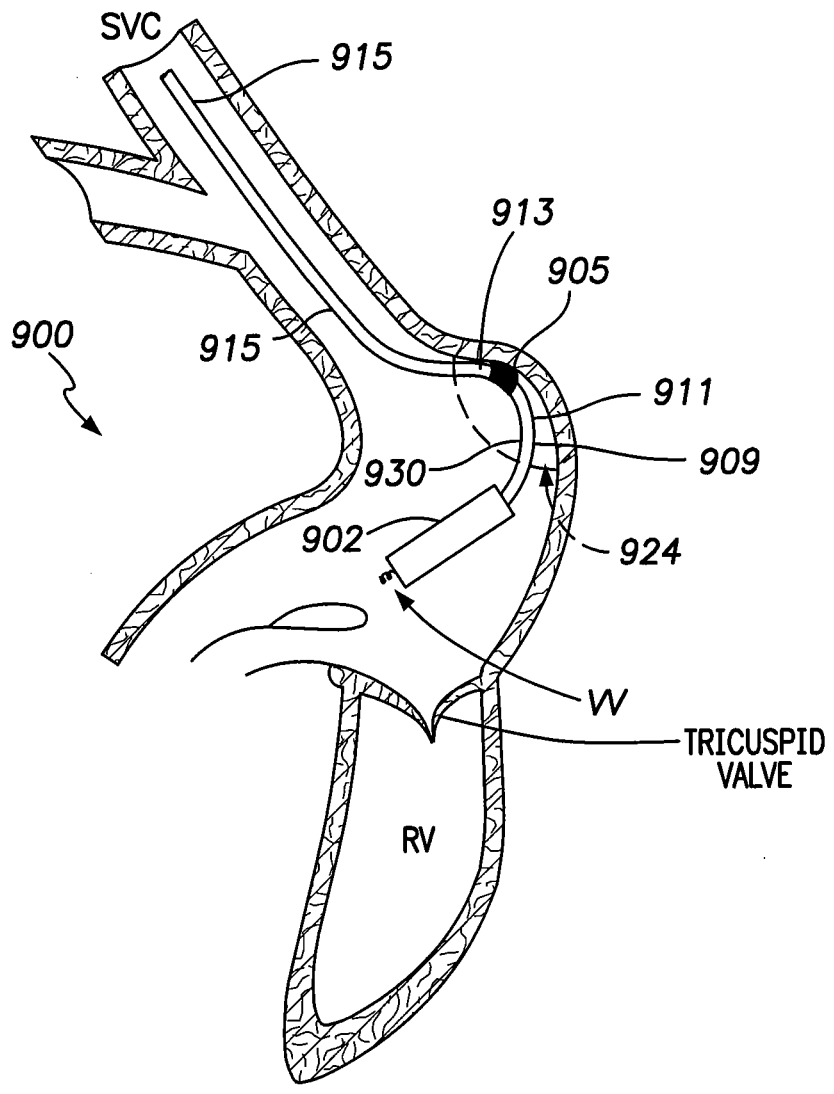
FIG. 9D further illustrates a model of an interior of a human heart and shows an example of the LIMD having the shaped IC device extension described with reference to FIG. 9A.
Figure 9E:
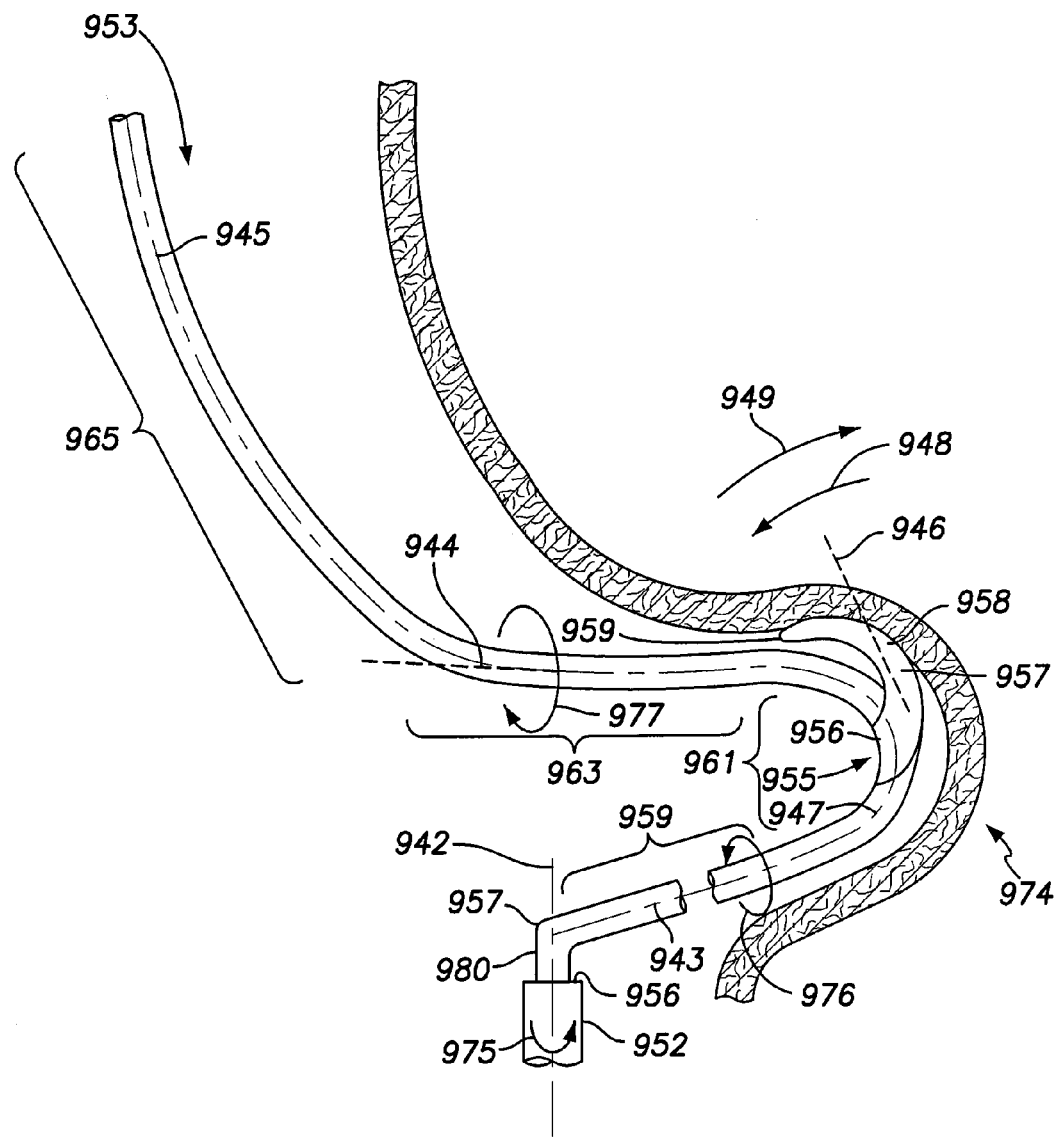
FIG. 9E provides an enlarged view of a portion of a shaped IC device extension, while in the right atrial appendage.

FIGS. 9C and 9D further illustrate a model of an interior of a human heart and shows an example of the LIMD 900 having the shaped IC device extension 903 described with reference to FIG. 9A. FIG. 9C generally illustrates an exemplary right lateral view of a heart, while FIG. 9D generally illustrates an exemplary anterior-posterior (AP) view. As points of reference, the RV vestibule 920, atrial IC device extension 924, and RV outflow track 922 are illustrated in one or both of FIGS. 9C and 9D. The AP view of FIG. 9D is oriented relative to the right lateral view of FIG. 9D, such that the viewer's line of sight (in FIG. 9D) is directed into the atrial IC device extension 924 along arrow 926 in FIG. 9C, whereas the viewer's line of sight in FIG. 9C is directed in the direction of arrow 928 in FIG. 9D.

The LIMD 900 is shown to be actively affixed near the RV vestibule 920. The views illustrated in FIGS. 9C and 9D are merely exemplary models of a potential three dimensional shape of the IC device extension 903. To further illustrate the 3D geometry of the IC device extension 903, planes 932-934 are shown in dashed line. The plane 932 generally follows X and Y axes that are defined with respect to the orientation of the housing 902. For example, the Y axis may correspond to the longitudinal axis of the housing 902. The plane 933 generally follows X and Z axes, wherein the X axis is oriented laterally with respect to the longitudinal axis of the housing 902 (e.g., from left to right across the drawing sheet). The Z axis is oriented transversely with respect to the longitudinal axis of the housing 902 and the lateral X axis (e.g., in and out of the drawing sheet).

The plane 932 (also referred to as the LIMD plane) is generally defined by the longitudinal axis of the housing 902, and a lateral axis along which the first linear region 909 extends. The plane 933 (also referred to as the RAA plane) is generally defined by the lateral axis along which the first linear region 909 extends and the transverse axis along which the second linear region 913 extends. The plane 934 (also referred to as the stabilization or SVC plane) is generally defined by the transverse axis along which the second linear region 913 extends and a stabilization path along which the third curved region 915 extends.

FIG. 9E provides an enlarged view of a portion of a shaped IC device extension 953, while in the right atrial IC device extension 974, accordance with an alternative embodiment. The shaped IC device extension 953 includes a short stem 980 that extends a short distance from the distal top end 906 of the housing 952 of an LIMD. The stem 980 merges into a first curved segment 957 that turns at a sharp angle with respect to a longitudinal axis 942 of the housing 902. Optionally, the first curved segment 957 may form an acute angle, a 90 degree angle, or an obtuse angle approximately with respect to the longitudinal axis 942 of the housing 952. The first curved segment 957 merges into and is followed by a first generally linear region 959 that extends laterally from the housing 902, along a lateral axis 943, until merging with a second curved segment 961. The second curved segment 961 turns at a compound sharp angle with respect to the longitudinal axis 942 of the housing 952 and the lateral axis 943 of the first linear region 959. Optionally, the second curved segment 961 may form an acute angle, a 90 degree angle, or an obtuse angle approximately with respect to the lateral axis 943 of the first linear region 959. As one example, the second curved segment 961 may approximate a 180 degree sharp or "hairpin" curve away from the lateral axis 943 of the first linear region 959 and away from the longitudinal axis 942 of the housing 952. The second curved segment 961 merges into, and is followed by, a second generally linear region 963 that extends along a second lateral direction 944.

One or more electrodes 955 are located along the second curved segment 961. Optionally, the electrode(s) 955 may be provided in the region proximate to the junction 951 of the second curved segment 961 and the second linear region 963. Optionally, one or more electrodes 955 may be provided along the second linear region 963. The electrode 955 includes a bracket ring 956 that at least partially surrounds the perimeter of the body of the shaped IC device extension 903. The bracket ring 956 is formed with a spring arm 957 that includes an outer bend 958 that terminates at a distal tip 959.

The second curved segment 961 follows an arcuate path 947, while the spring arm 957 extends outward from the arcuate path 947 in a tangential direction 946 to form an acute angle with the second lateral axis 944. The distal tip 959 may be directed inward toward the second linear region 963 such as to avoid damaging wall tissue. The spring arm 957 pivots, relative to the second curved segment 961 and relative to the second linear segment 963, inward and outward along arrow 948 and 949. The spring arm 957 is biased outward in the direction of arrow 949 to a normal resting position. When implanted, the tissue wall places a load against, and slightly deflects, the spring arm 957 inward along arrow 948, thereby affording constant and steady contact between the electrode 955 and the tissue wall in the right atrial IC device extension 974.

The second linear region 963 merges with and extends to a third curved segment 965. The third curved segment 965 follows an extending "slow" arc and then terminates at a tail end of the IC device extension 953. The third curved segment 965 follows a slow arc, along an arcuate path 945, with respect to the longitudinal axis 942 of the housing 952 and the first and second lateral axes 943 and 944 of the first and second linear regions 959 and 963.

The lateral axis 943 of the first linear region 959 projects from the longitudinal axis 942 at a yaw angle 975, where the yaw angle 975 is measured from a zero reference yaw angle about the longitudinal axis 942. The second curved segment 974 bends in a direction that projects from, or about, the lateral axis 943, at a roll angle 976, where the roll angle 976 is measured from a zero reference roll angle about the lateral axis 943. The second linear region 963 extends along the second lateral axis 944 at a complex angle with respect to the lateral axis 943. The third curved segment 965 projects from the second lateral axis 944, at a pitch angle 977 from a zero reference pitch angle about the second lateral axis 944.

It should be understood that the axes, directions, curves, and linear paths followed by the regions and segments of the shaped IC device extension 903 of FIG. 9A may resemble or differ from the axes, directions, curves, and linear pathes followed by the regions and segments of the shaped IC device extension 953 of FIG. 9E.

Figure 9F:
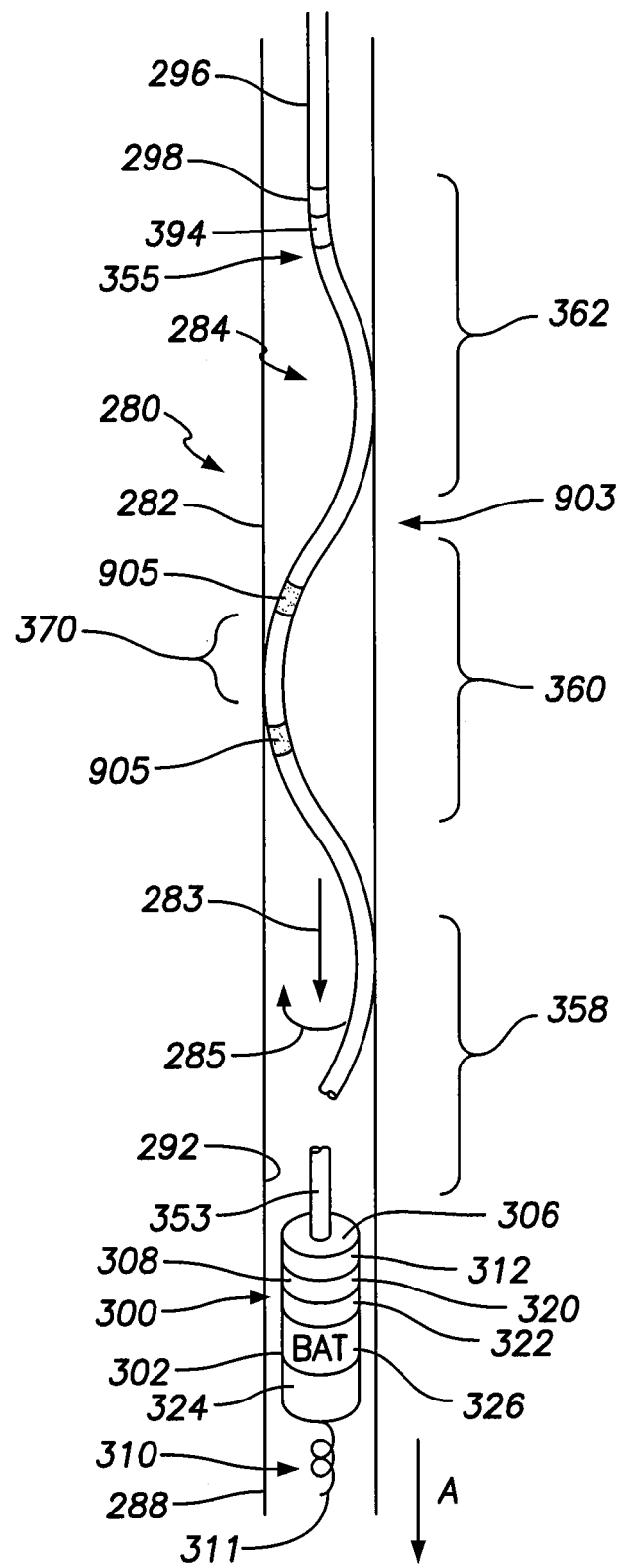
FIG. 9F illustrates a longitudinal axial view of an introducer assembly, with the LIMD including the IC device extension of FIG. 9A inserted therein.

FIG. 9F illustrates a longitudinal axial view of an introducer assembly 280, formed according to an embodiment with the LIMD 900 including the IC device extension 903 of FIG. 9A inserted therein. The IC device extension 903 includes an extension body having a proximal end 353. The introducer assembly 280 includes a flexible, longitudinal, cylindrical open-ended sheath 282 defining a central internal passage 284. The sheath 282 may be a flexible tube formed of rubber, for example, that is configured to be maneuvered through patient anatomy, such as veins and the heart. In this respect, the sheath 282 may be similar to that of a cardiac catheter.

A physician or surgeon operates user controls on the introducer assembly 280 at a proximal end (not shown). The proximal end may include user controls that allow the sheath 282 to be bent, curved, canted, rotated, twisted, or the like, so as to be navigated through a patient's vasculature. For example, a distal end 288 of the sheath 282 may be bent, curved, canted, rotated, twisted, articulated, or the like through operation by the physician or surgeon manipulating the user controls at the proximal end of the assembly 280.

The LIMD 900 is held in the distal end 288 of the sheath 282. As shown, the housing 902 of the LIMD 900 slides along inner walls 292 of the sheath 282. The LIMD 900 is configured to be pushed out of, or ejected from, the sheath 282 in the direction of arrow A. The top end 906 of the LIMD 900 connects to the IC device extension 903. The proximal end 353 of the IC device extension 903 is coupled to the housing 902 of the LIMD 900. The extension body extends between the proximal end 353 and a distal end 355. The extension body including a transition sub-segment 357, an active interim-segment 360 and a stabilizer end-segment 362, all of which are "stretched out" or elongated to extend generally along the length of the internal passage 284 of the sheath 282.

With cross-reference to FIGS. 9A-9E, the transition sub-segment 357 generally includes the stem 930, first curved segment 907 and at least a portion of the first linear region 909. The active interim-segment 360 includes the second curved segment 911, and may include portions of the first and second linear regions 909 and 913. The stabilizer end-segment 362 includes the third curved segment 915 and may include a portion of the second linear region 913. It should be recognized that the correlation between the segments and regions of FIGS. 9A-9E and the transition sub-segment 357, active interim-segment 360 and stabilizer end-segment 362, are exemplary implementations. Similarly, the transition sub-segment 357, active interim-segment 360 and stabilizer end-segment 362 may be correlated to the stabilization arms and appendage arms described in connection with the embodiments of FIGS. 5-7.

The extension body is formed of materials that are flexible, yet offer good shape memory such that the extension body may be stretched out while within the sheath 282 and, when removed from the sheath 282, then return to its original (normal, resting) shape as shown in FIG. 1A. For example, the extension body may be formed of silicon that is cured to desired crosslink structure that holds (or is biased to return to) a pre-loaded shape (e.g., through a thermal set process).

In the example shown in FIG. 9F, the active interim-segment 360 (e.g., corresponding to second curved segment 911) is straightened to remove the curved shape only while in the sheath 282. Similarly, the stabilizer end-segment 362 (e.g., corresponding to the third curved segment 915) is straightened. While the example of FIG. 9F illustrates a slight wave or curve that remains in the extension body, optionally, the extension body may be constrained to be much straighter or permitted to remain even more curved or bent. The amount to which the active interim-segment 360 and stabilizer end-segment 362 are straightened or curved may vary depending upon the outer dimensions of the extension body and the inner dimensions of the sheath 282.

A pusher rod 296 is provided to be slidably inserted into the sheath 282 in order to manipulate the IC device extension 903 and LIMD 900. For example, the pusher rod 296 may linearly translate the IC device extension 903 and LIMD 900 along the longitudinal axis 283 and rotate the IC device extension 903 and LIMD 900 about the rotational axis 285. The pusher rod 296 includes a pusher tip connector 298 that is configured to securely engage the distal end 355 of the extension body. The distal tip 355 includes a connection member 394 that is configured to securely mate with the pusher tip connector 298 (e.g., through a threaded connection, an interference fit, or the like). The pusher rod 296 may extend into and retract from the sheath 282 under a physician's control. The pusher rod 296 and LIMD 900 are located at opposite ends of the extension body. However, rotational force applied by the pusher rod 296 on the distal end 355 of the extension body is substantially all transferred to the LIMD 900. This rotational force may be used to actively secure the LIMD 900 to the wall tissue through the active fixation member, such as a helical anchor, a coil, a helical wire having a sharp point, a hook, a barb, or the like.

FIG. 9F also illustrates the general internal components of the LIMD 900. The housing 902 include a charge storage unit 324 and a battery 326 that supplies power to the electronics and energy to the charge storage unit 324. The housing 302 also includes a sensing circuit 322 and a controller 320.

The sensing circuit 322 senses intrinsic activity, while the change storage unit 324 stores high or low energy amounts to be delivered in one or more stimulus pulses. Electrodes 311, 905 may be used to deliver lower energy or high energy stimulus pulses, such as pacing pulses, cardioverter pulse trains, defibrillation shocks and the like. The electrodes 311, 905 may also be used to sense electrical activity, such as physiologic and pathologic behavior and events and provide sensed signals to the sensing circuit 322. The electrodes 311, 905 are configured to be joined to an energy source, such as the charge storage unit 324. The electrodes 311, 905 receive stimulus pulse(s) from the charge storage unit 324. The electrodes 311, 905 may be the same or different size.

The controller 320, within the housing 302, controls the overall functionality of the LIMD 900 including causing the charge storage unit 324 to deliver activation pulses through each of the electrodes 311, 905 in a synchronous manner, based on information from the sensing circuit 322, such that activation pulses delivered from the electrode 311 are timed to initiate activation in the adjacent chamber, while activation pulses delivered from the electrodes 905 are timed to initiate activation in the local chamber. The stimulus pulses are delivered synchronously to local and distal activation sites in the local and distal conduction networks such that stimulus pulses delivered at the distal activation site are timed to cause contraction of the adjacent chamber in a predetermined relation to contraction of the local chamber. The electrodes 311, 905 are spaced radially and longitudinally apart from one another such that the local activation site (e.g., right atrium) and the distal activation side in the adjacent chamber (e.g., right ventricle) are sufficiently distant from one another within the heart's conductive network to initiate activation in different branches of the hearts conductive network in a time relation that corresponds to the normal hemodynamic timers (e.g. AV delay).

The controller 320 may operate the LIMD 900 in various modes as discussed herein. The sensing circuit 322 receives sensed signals from one or more of the electrodes 311, 905. When pairs of electrodes are provided in the location of electrode 311 or in the location of electrode 905, the sensing circuit 322 discriminates between sensed signals from respective pairs of electrodes that originate in the near field and in the far field. For example, a pair of electrodes 905 may sense electrical potential across small areas and thereby allow the sensing circuit 322 to discriminate between different sources of electrical signals. In one embodiment, the inter-electrode gap 370 between electrodes 905 is limited or minimized in order to achieve a select type of sensing such as bipolar sensing which limits or minimizes sensing of far field signals. With a small inter-electrode gap or separation 370, when far field signals (e.g., signals from the right ventricle, left atrium or left ventricle) reach the electrodes 905 these far field signals are sensed as a common mode signal with no or a very small potential difference between the electrodes. Similarly, if a pair of electrodes 311 are provided on the active fixation member 310, the electrodes 311 may be separated by a small inter-electrode gap such that, when far field signals (e.g., signals from the right atrium or left ventricle) reach the electrodes 311 these far field signals are sensed as a common mode signal with no or a very small potential difference between the electrodes.

Optionally, an electrode 312 may be provided on the housing 302 and operate as an anode electrode, while the electrode 311 and/or electrodes 905 may operate as cathode electrodes. When an anode electrode 312 is provided on the housing 302, the controller 320 may be configured to cause stimulus pulses to be delivered between the anode electrode 312 and the first electrode 311 to stimulate the local chamber. When an anode electrode 312 is provided on the housing 302, the sensing circuit 312 may be configured to sense between the anode 312 and the second electrode 905 or 311.

Figure 9G:
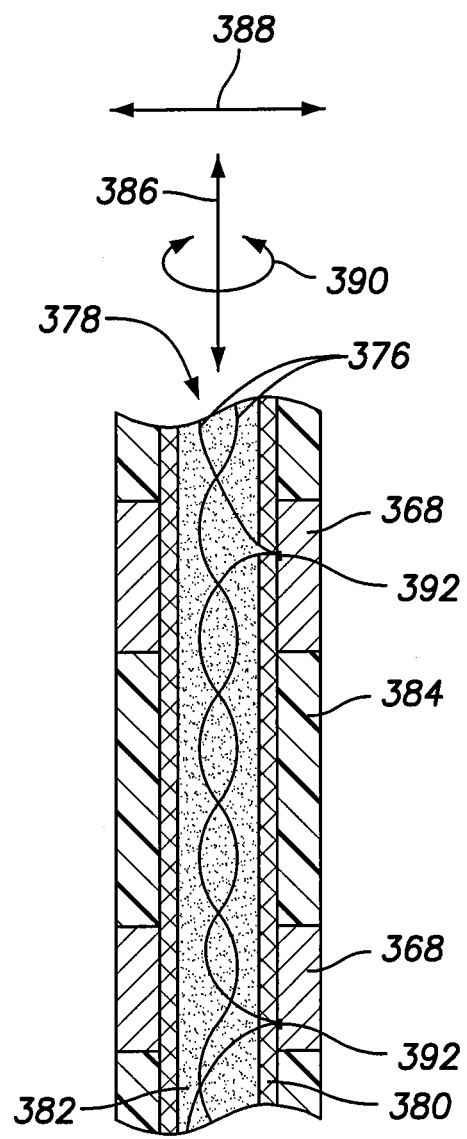
FIG. 9G illustrates a cross section of a portion of an IC device extension according to an embodiment.

FIG. 9G illustrates a cross section of a portion of the IC device extension of FIGS. 9A-9E. Optionally, FIG. 9G may also represent the cross section of the appendage arm of FIGS. 5A to 7B or the stabilization arm of FIGS. 5A to 7B but with the electrodes and insulated conductors removed. The IC device extension 360 includes one or more insulated conductors 376 that are connected to corresponding electrodes 368. The conductors 376 are connected through a switch to electronics within the LIMD 900 to perform sensing and/or deliver stimulus pulses. The conductors 376 may be wound about one another in a helical manner. The conductors 376 extend along a core 378 and the conductors 376 are radially surrounded by an elongated braid 380. The braid 380 may be made of steel or wire mesh, or have a honeycomb pattern that resists compression or IC device extension along the length of the IC device extension body (as denoted by longitudinal direction 386). The braid 380 is flexible in a lateral direction 388 in order to be bent side to side during implant and following implant. The mesh or honeycomb configuration of the braid 380 affords strong resistance to torque about the length of the IC device extension body when turned in the rotational direction 390 about the longitudinal direction 386. It is desirable to be resistant to torque in order that, during implant, when a rotational force is applied to one end of the IC device extension body, substantially all of such rotational force is conveyed along the length of the IC device extension body to the opposite end. As explained hereafter, the braid 380 facilitates delivery of rotational forces and longitudinal pressure to the LIMD 900 and the active fixation member during implant.

Optionally, the IC device extension body may further includes an insulation material 382 provided around the conductors 376 and around the braid 380. An insulated, flexible, biocompatible shell 384 is formed over the braid 380. The electrodes 368 are connected to separate corresponding conductors 376 at contacts 392. The electrodes 368 may be formed as ring electrodes, coil electrodes, pin or bump electrodes and the like. While two electrodes 368 are illustrated it is understood that only one or more than two electrodes 368 may be provided on the IC device extension body. The electrodes 368 may be provided at various points about the perimeter of the IC device extension body and at multiple points along the length of the IC device extension body.

The electrodes 368 are separated from the braid 380 by insulation (e.g. part of the shell 384). The electrodes 368, braid 380 and conductors 376 may be arranged concentrically with one another in a coaxially configuration.

Figure 10:
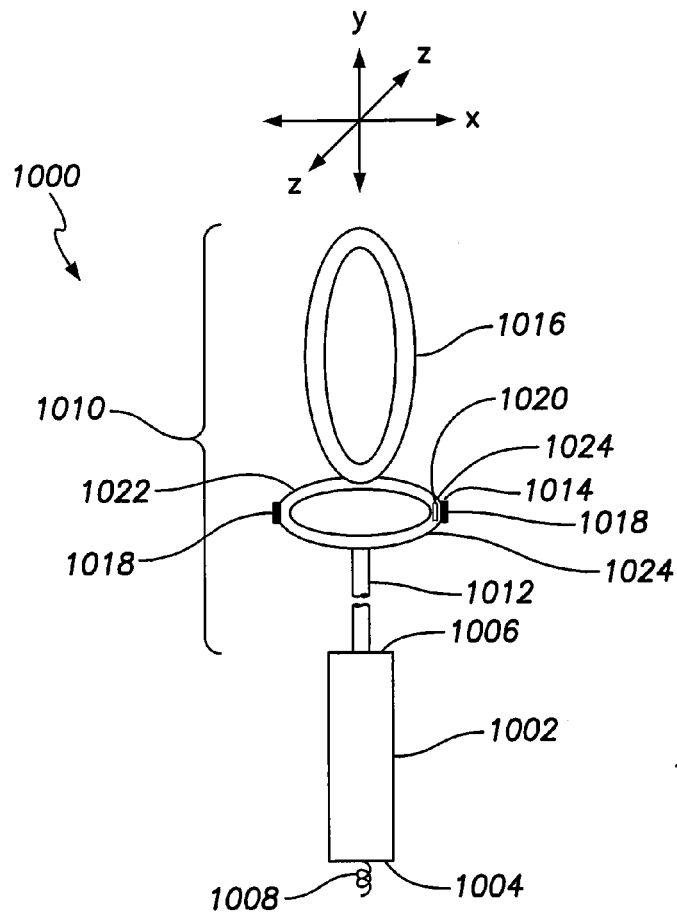
FIG. 10 illustrates an embodiment of a LIMD.

FIG. 10 illustrates a LIMD 1000, according to an embodiment. The LIMD includes a housing 1002 having a heart-wall securing base 1004 and a top or proximal end 1006. An anchoring member, such as a securing helix 1008, which may be formed of a conductive material, such as metal, extends from the base 1004 of the housing 1002 and is configured to securely anchor the housing 1002, and therefore the LIMD 1000, to tissue within a chamber of a heart. The securing helix 1008 may also serve as an electrode. Instead of the securing helix 1008, a barb, hook, or the like may extend from the housing 1002. Additionally, the anchoring member may be any of the securing configurations shown in FIGS. 4A-G.

The proximal end 1006 of the housing 1002 connects to a stabilizing IC device extension 1010 having a stabilizing loop member. The stabilizing loop member of the stabilizing IC device extension 1010 may include a linear beam 1012 that connects to a first or inner loop 1014 that, in turn, connects to a second or outer loop 1016. The outer loop 1016 is distally located from the housing 1002. Alternatively, the IC device extension 1010 may not include the linear beam 1012, but instead may include just the loops 1014 and 1016 that join directly to the housing 1002. Additionally, more or fewer loops than shown may be used. For example, the LIMD 1000 may include only one loop, or the LIMD 1000 may include three or more loops.

The inner and outer loops 1014 and 1016 each have a perimeter that may be flared (for example, diverges and then re-merges) in a direction generally toward and away from the lateral axis X which extends in a lateral direction with respect to the longitudinal axis Y of the loops 1014 and 1016 and housing 1002. The inner and outer loops 1014 and 106 may have different contoured shapes, as shown in FIG. 10. By way of example, the loops 1014 and 1016 may have a perimeter, when viewed from the top down, that is disc-shaped, oval, circular, tubular, rectangular, triangular, and the like.

The loops 1014 and 1016 have opposed top and bottom sides that are aligned generally in parallel planes that extend in a generally common direction as the longitudinal axis Y. The loops 1014 and 1016 are aligned along a common path. Alternatively, the loops 1014 and 1016 may be oriented in a different manner with respect to one another. For example, the loops 1014 and 1016 may be oriented orthogonal to one another, such that the loop 1014 is oriented in a plane defined by the X and Y axes, while the loop 1016 is oriented in a plane defined by the Y and Z axes, or vice versa. Moreover, it is recognized that, while FIG. 10 illustrates the loops 1014 and 1016 aligned in a straight manner, this is for illustration purposes. When implanted, the loops 1014 and 1016 will curve and wrap to follow the contour of an interior of the heart in a manner determined by the implanting physician. The loops 1014 and 1016 are shown in FIG. 10 in a deployed implanted shape, but are flexible and are compressed into a collapsed installation shape while being installed.

Electrodes 1018 are secured to the inner loop 1014 on either side and are configured to contact interior wall portions of the superior vena cava of the heart. A radio marker 1020 may be secured next to an electrode 1018. Although the electrodes 1018 are shown on the inner loop 1014, the electrodes 1018 may be positioned on the outer loop 1016. Alternatively, each loop 1014 and 1016 may have one or more electrodes.

The electrodes 1018 are spaced apart from one another by an inter-electrode spacing (for example, the diameter of the loop segment 1014). The electrodes 1018 may be wrapped around, or otherwise secured to, a peripheral portion of the inner loop 1014. As shown in FIG. 10, two electrodes 1018 are secured around circumferential portions of the inner loop 1018 at diametrically opposite sides 1022 and 1024.

The inner and outer loops 1014 and 1016 are joined to one another at connection links or joints. As shown, the electrodes 1018 are distally located from one another on the inner loop 1014 and may be positioned generally at a radial angle θ that is 90° from the connection link or joint with outer loop 1016, for example. The opposed electrodes 1018 are configured to contact tissue portions within a heart. The number of electrodes 1018 may vary depending on a particular application. For example, additional electrodes may be secured to the inner and/or outer loops 1014 and 1016. Additionally, while the electrodes 1018 are shown at opposite sides 1022 and 1024 of the inner loop 1014, the electrodes 1018 may be positioned at various other locations on the inner loop 1014, and even at different locations from the connection joint. Also, more or less electrodes 1018 than those shown on the inner loop 1014 may be used. For example, the inner loop 1014 may include only one electrode 1018.

The electrodes 1018 may be used to deliver low energy or high energy stimulus, such as pacing pulses, cardioverter pulse trains, defibrillation shocks and the like. The electrodes 1018 may also be used to sense electrical activity, such as physiologic and pathologic behavior and events.

The dual-loop IC device extension 1010 includes shape memory characteristics that allow the inner and outer loops 1014 and 1016 to transform between collapsed states, in which the loops 1014 and 1016 assume a substantially flat or compressed shape, and an expanded deployed state, in which the loops 1014 and 1016 assume a more rounded loop shape. In an alternate configuration one or both of the loops may have an open configuration provided by a break in loop continuity along the perimeter of the loop.

The radio marker 1020 may be used to determine the position of the inner loop 1014 within patient anatomy. For example, the radio marker 1020 may be used in conjunction with an electromagnetic surgical navigation system and an imaging device, such as a fluoroscope, to track the position of the LIMD 1000 within patient anatomy. For example, a fluoroscope may image the patient anatomy. The position of the radio marker 1020 may then be registered with respect to the fluoroscopic images. Thus, as the LIMD 1000 moves within the patient anatomy, a display showing the fluoroscopic image(s) and a representation of the LIMD 1000 may track movement of the LIMD 1000 through movement of the radio marker 1020, which was previously registered with the fluoroscopic image(s).

While one radio marker 1020 is shown, more radio markers may be used. For example, radio markers may be secured to both loops 1014 and 1016 and/or the linear beam 1012. Alternatively, the LIMD 1000 may not include a radio marker.

Figure 11:
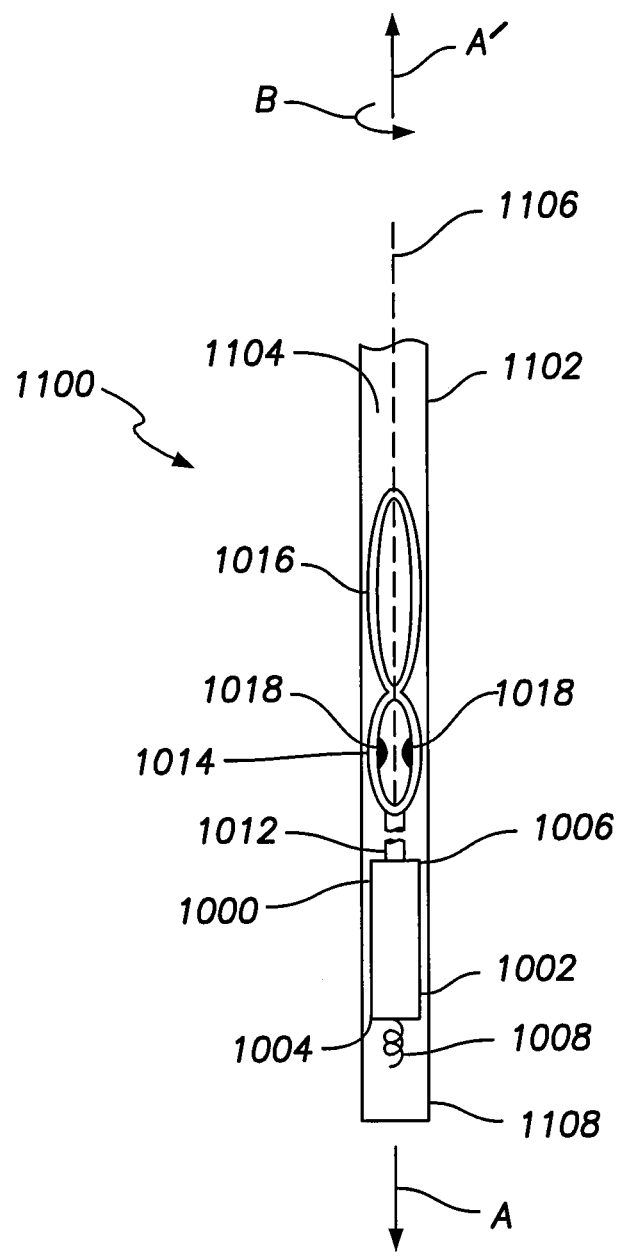
FIG. 11 illustrates a LIMD introducer assembly with the LIMD of FIG. 10 inserted therein.

FIG. 11 illustrates an LIMD introducer assembly 1100, according to an embodiment. The introducer assembly 1100 includes a flexible tube, sheath, or the like 1102, such as a catheter, having an internal longitudinal passage 1104 into which the LIMD 1000, including the loops 1014, 1016 and the housing 1002, are retained. The introducer assembly 1100 is maneuvered by a physician at a proximal end (not shown) into a heart of a patient such that the housing 1002 is positioned in a lower region of the right atrium between the OS and IVC. The housing 1002 is anchored in place through the securing helix 1008.

As shown in FIG. 11, the inner and outer loops 1014 and 1016 of the LIMD 1000 are collapsed or compressed within the flexible tube 1102 into a collapsed installation shape. This arrangement is designed to prevent premature deployment of the LIMD 1000 and prevent damage to vascular access ways for implantation. A pusher implant tool 1106 affixes to the proximal end 1006 of the housing 1002 and may use hooks or expanding collets to lock into inner loop 1014. The introducer assembly 1100 is designed to be steerable so that the LIMD 1000 can be finely navigated to the desired implant site.

Once the implantation site in the right atrium is located (via fluoroscopy, echocardiography, or other means), a distal end 1108 of the introducer assembly 1100 is positioned at the implantation site and the pusher implant tool 1106 is pushed in the direction of arrow A to place the securing helix 1008 adjacent tissue. The pusher implant tool 1106 is then rotated in the direction of arc B. The rotation translates to the housing 1002 and in turn to the securing helix 1008. The securing helix 1008, which as noted above may also serve as an electrode, extends into the myocardium through the right atrium, causing it to drill into ventricular tissue that bounds the right atrium. Then, the fidelity of the implantation process may be verified by ventricular capture and sensing tests.

Next, the introducer assembly 1100 is retracted enough to allow the inner loop 1014 to extend out of the sheath in the region of the high right atrium at the SVC/RA junction. The steerable introducer assembly 1100 is adjusted to have the radio marker 1020 (shown in FIG. 10) located at the desired location and the inner loop 1014 in good contact with atrial tissue.

Finally, the introducer assembly 1100 is further retracted relative to the LIMD 1000 until the outer loop 1016 passes out of the tube 1102. That is, the introducer assembly 1100 is pulled back in the direction of arrow A', leaving the housing 1002 secured to the heart 12 within the right atrium. The introducer assembly 1100 disengages from the LIMD 1000 as the introducer assembly 1100 is pulled away in the direction of arrow A'. Accordingly, the outer loop 1016 expands until it reaches the inner diameter of the SVC. The pusher tool 1106 is then disengaged from the housing 1002 and/or the first loop 1014.

Figure 12:
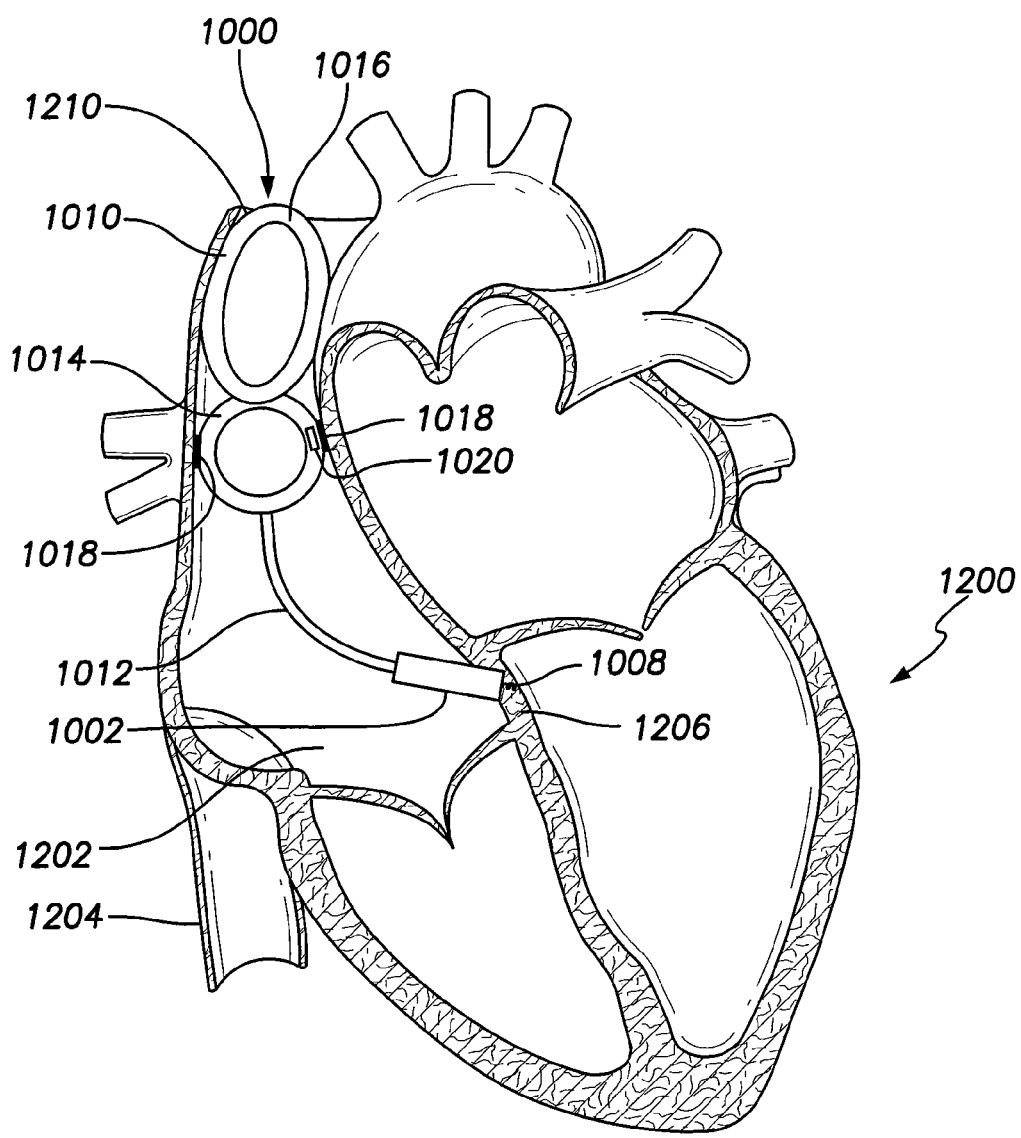
FIG. 12 illustrates the LIMD of FIG. 10 implanted within a heart of a patient.

FIG. 12 illustrates the LIMD 1000 implanted within a heart 1200 of a patient, according to an embodiment. The LIMD 1000 is implanted entirely within the heart 1200. The LIMD 1000 is configured to place the housing 1002 in the lower region of the right atrium 1202 between the OS and the IVC 1204 with the securing helix 1008 in the ventricular vestibule 1206 to provide ventricular pacing and sensing. The LIMD 1000 is further configured such that the dual-loop IC device extension 1010 extends upward in the right atrium 1202 toward and into the SVC 1210. The dual-loop IC device extension 1010 is configured (length-wise and shape-wise) such that the inner loop 1014 may be implanted in the upper region of the right atrium 1202 near the junction of the right atrium 1202 and the SVC 1210. As shown, the electrodes 1018 are compressed into inner walls of the heart 1200 proximate the junction of the SVC 1210 and the right atrium 1202. As such, the inner loop 1014 in the right atrium is configured for right atrial pacing and sensing. When in its expanded state, the inner loop 1014 has an outer diameter greater than the inner diameter of the SVC 1210.

As shown, the outer loop 1016 is secured within the heart 1200 such that the majority of the outer loop 1016 is positioned within the SVC 1210 to provide passive mechanical stabilization of the LIMD 1000. When in its expanded state, the outer diameter of the outer loop 1016 is greater than the inner diameter of the SVC 1210.

Figure 13:
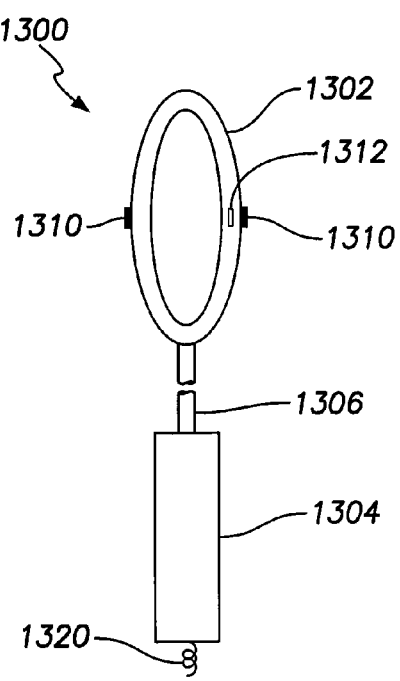
FIG. 13 illustrates another embodiment of an LIMD.

FIG. 13 illustrates a LIMD 1300, according to an embodiment. The LIMD 1300 is similar to the LIMD 1000 shown and described with respect to FIG. 10, except that the LIMD 1300 includes a stabilizing loop member having a single loop 1302 connected to a housing 1304 through a linear beam 1306. Alternatively, instead of using a linear beam, the single loop 1302 may connect directly to the housing 1304. A securing helix 1320 extends from a base of the housing 1304. Electrodes 1310 are positioned on outer portions of the loop 1302, as discussed above, and a radio marker 1312 may also be positioned on the loop 1302. The single loop 1302 anchors the LIMD 1300 within a local chamber of the heart, such as the right atrium.

Figure 14:
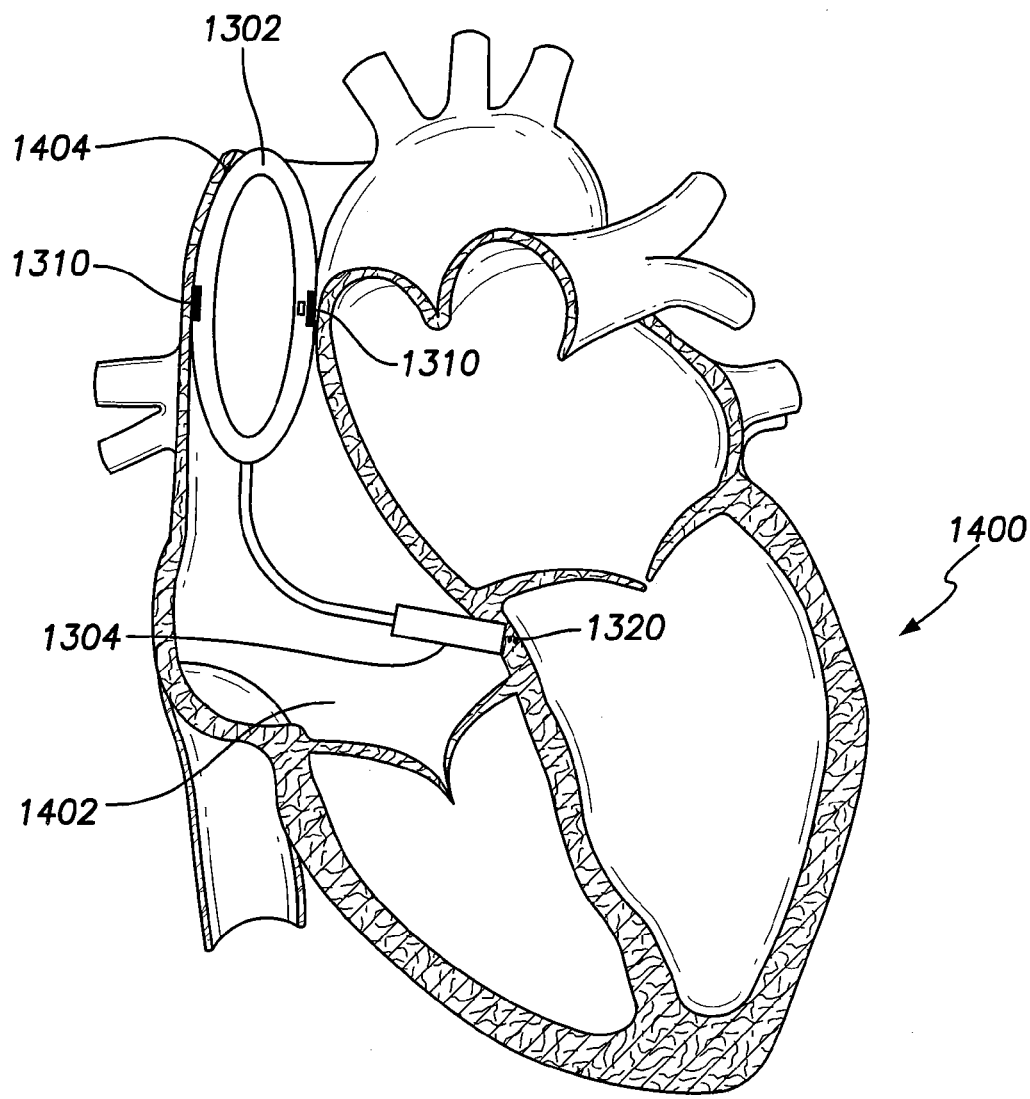
FIG. 14 illustrates the LIMD of FIG. 13 implanted within a heart of a patient.

FIG. 14 illustrates the LIMD 1300 implanted within a heart 1400 of a patient, according to an embodiment. The housing 1304 is contained within the right atrium 1402. The single loop 1302 is secured within the SVC 1404 such that the electrodes 1310 are compressed into inner walls of the SVC 1404. The securing helix 1320 is anchored into the tissue of the right atrium 1402, as discussed above.

As shown in FIGS. 12 and 14, embodiments provide an LIMD that may be contained within the right atrium such that the housing is entirely within the right atrium and the IC device extension is passively secured within the SVC and/or a junction of the SVC and right atrium. Alternatively, the LIMD may be contained within any other local chamber. For example, the housing may be secured within the right ventricle, while the IC device extension is passively secured within the SVC and/or a junction of the SVC and right atrium.

As explained above, embodiments provide a LIMD that is compact and configured to be retained within a chamber of the heart. Embodiments herein utilize an intra-cardiac implantable medical device having securing IC device extension that is pre-formed into planar disc-shaped segments, such as loops. The IC device extension is coupled to a housing of the LIMD. The LIMD is configured to be positioned within a local chamber of the heart, with the IC device extension extending into, and being passively anchored within, the SVC, for example. For example, the housing of the LIMD may be completely contained within the right atrium of the heart.

Optionally, droplets or small amounts of a steroid may be added at select points along the IC device extension and LIMD to promote tissue growth.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A leadless intra-cardiac medical device configured to be implanted entirely within a heart of a patient, the device comprising:
    a housing configured to be securely attached to an interior wall portion of a chamber of the heart, the housing having a proximal end and a distal end, and the housing hermetically enclosing electronics, a controller, and a battery;
    a securing device extending from the proximal end of the housing, the securing device configured to secure the housing to cardiac tissue;
    an appendage arm extending from the distal end of the housing, the appendage arm having a proximal end directly connected to the distal end of the housing, and the appendage arm having a distal end upon which an electrode is disposed;
    a stabilizer arm extending from the distal end of the housing, the stabilizer arm having a proximal end directly connected to the distal end of the housing, and the stabilizer arm having a distal end upon which a pusher cup is disposed.

2. The device of claim 1, wherein the appendage arm is rotatably connected to the distal end of the housing by a first hinge assembly, and wherein the stabilizer arm is rotatably connected to the distal end of the housing by a second hinge assembly.

3. The device of claim 1, wherein the appendage arm is fixedly secured to the distal end of the housing, wherein a body of the appendage arm comprises a flexibly material having a desired preformed resting shape that is non-linear, wherein the stabilizer arm is fixedly secured to the distal end of the housing, and wherein a body of the stabilizer arm comprises a flexibly material having a desired preformed resting shape that is non-linear.

4. The device of claim 1, wherein the securing device is an active fixation helix.

5. The device of claim 1, wherein the appendage arm is rotatably connected to the distal end of the housing by a first hinge assembly, and wherein the stabilizer arm is rotatably connected to the distal end of the housing by a second hinge assembly.

6. The device of claim 1, wherein the pusher cup has a pusher receptacle.

7. The device of claim 6, wherein the pusher receptacle has a threaded recess configured to threadably receive a top of a pusher tool.

8. The device of claim 1, wherein the stabilizer arm has a core structure that is torque and compression resistant.

9. The device of claim 1, wherein the appendage arm has a core structure that is torque and compression resistant.

* * * * *